(12) United States Patent
Asirvatham et al.

(10) Patent No.: US 10,973,573 B2
(45) Date of Patent: Apr. 13, 2021

(54) DEVICE AND METHOD FOR TREATING CARDIAC DISORDERS BY MODULATING AUTONOMIC RESPONSE

(71) Applicant: Mayo Foundation for Medical Education and Research, Rochester, MN (US)

(72) Inventors: Samuel J. Asirvatham, Rochester, MN (US); Mark B. Knudson, Shoreview, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 58 days.

(21) Appl. No.: 16/196,473

(22) Filed: Nov. 20, 2018

(65) Prior Publication Data

US 2019/0090946 A1 Mar. 28, 2019

Related U.S. Application Data

(63) Continuation of application No. 15/184,379, filed on Jun. 16, 2016, now abandoned, which is a
(Continued)

(51) Int. Cl.
*A61N 1/05* (2006.01)
*A61N 1/20* (2006.01)
(Continued)

(52) U.S. Cl.
CPC ........ *A61B 18/1492* (2013.01); *A61B 5/0215* (2013.01); *A61B 5/04001* (2013.01);
(Continued)

(58) Field of Classification Search
CPC combination set(s) only.
See application file for complete search history.

(56) References Cited

U.S. PATENT DOCUMENTS 5,139,020 A 8/1992 Asirvatham et al.
5,515,682 A 5/1996 Nagakubo et al.
(Continued)

FOREIGN PATENT DOCUMENTS

WO WO1995001751 1/1995
WO WO2007079438 7/2007
(Continued)

OTHER PUBLICATIONS

Armour et al., "Gross and microscopic anatomy of the human intrinsic cardiac nervous system," Anat Rec., 247(2):289-298, Feb. 1997.
(Continued)

*Primary Examiner* — Jon Eric C Morales
(74) *Attorney, Agent, or Firm* — Fish & Richardson P.C.

(57) ABSTRACT

A method and device for modulating the autonomic nervous system adjacent a pericardial space to treat cardiac arrhythmia includes a treatment source arranged to supply a treatment medium, a catheter having an end sized for insertion into the pericardial space, a medium delivery assembly having a distal end arranged to be positioned by the catheter into the pericardium, with the distal end of the delivery assembly comprising a delivery tip arranged to extend away from the distal end of the catheter into the pericardial space. A connector operatively couples the delivery tip of the medium delivery assembly to the treatment source, and the delivery tip of the medium delivery assembly including a plurality of delivery points for delivering the treatment medium at a plurality of treatment areas within the pericardial space. The device performs modulation or ablation of the autonomic nervous system at selected treatment areas within the pericardium.

17 Claims, 10 Drawing Sheets

Related U.S. Application Data continuation of application No. 13/515,630, filed as application No. PCT/US2010/058950 on Dec. 3, 2010, now Pat. No. 9,392,971.

(60) Provisional application No. 61/286,303, filed on Dec. 14, 2009.

(51) Int. Cl.
| | |
|---|---|
| A61B 18/14 | (2006.01) |
| A61B 5/0215 | (2006.01) |
| A61B 5/04 | (2006.01) |
| A61B 5/0402 | (2006.01) |
| A61B 18/02 | (2006.01) |
| A61M 25/00 | (2006.01) |
| A61M 25/04 | (2006.01) |
| A61M 25/10 | (2013.01) |
| A61B 5/00 | (2006.01) |
| A61N 1/36 | (2006.01) |
| A61B 5/02 | (2006.01) |
| A61B 18/00 | (2006.01) |
| A61N 1/06 | (2006.01) |

(52) U.S. Cl.
CPC .......... *A61B 5/0402* (2013.01); *A61B 5/4035* (2013.01); *A61B 18/02* (2013.01); *A61M 25/007* (2013.01); *A61M 25/04* (2013.01); *A61M 25/10* (2013.01); *A61N 1/0587* (2013.01); *A61N 1/20* (2013.01); *A61N 1/36114* (2013.01); *A61B 5/02* (2013.01); *A61B 2018/0022* (2013.01); *A61B 2018/00083* (2013.01); *A61B 2018/00214* (2013.01); *A61B 2018/00351* (2013.01); *A61B 2018/00434* (2013.01); *A61B 2018/00577* (2013.01); *A61B 2018/00839* (2013.01); *A61B 2018/00994* (2013.01); *A61B 2218/002* (2013.01); *A61M 2025/105* (2013.01); *A61N 1/06* (2013.01)

(56) References Cited

U.S. PATENT DOCUMENTS

| | | | |
|---|---|---|---|
| 5,830,213 A | 11/1998 | Panescu et al. | |
| 6,314,963 B1 | 11/2001 | Vaska et al. | |
| 6,371,955 B1 | 4/2002 | Fuimaono et al. | |
| 6,440,128 B1 * | 8/2002 | Edwards ............ | A61B 18/1485 606/41 |
| 6,471,696 B1 | 10/2002 | Berube et al. | |
| 6,511,500 B1 | 1/2003 | Rahme | |
| 6,595,959 B1 | 7/2003 | Stratienko | |
| 6,965,798 B2 | 11/2005 | Kim | |
| 7,322,973 B2 | 1/2008 | Nahon | |
| 7,399,300 B2 | 7/2008 | Bertolero et al. | |
| 7,429,261 B2 | 9/2008 | Kunis et al. | |
| 7,449,018 B2 | 11/2008 | Kramer | |
| 7,567,841 B2 | 7/2009 | Chan | |
| 9,392,971 B2 | 7/2016 | Asirvatham et al. | |
| 2002/0161360 A1 | 10/2002 | Carroll | |
| 2002/0177765 A1 | 11/2002 | Bowe et al. | |
| 2003/0220636 A1 | 11/2003 | Bowman et al. | |
| 2004/0010290 A1 | 1/2004 | Scroeppel et al. | |
| 2004/0186468 A1 | 9/2004 | Edwards | |
| 2005/0059962 A1 | 3/2005 | Phan et al. | |
| 2005/0143378 A1 | 6/2005 | Yun et al. | |
| 2005/0171536 A1 | 8/2005 | Phan et al. | |
| 2005/0209668 A1 | 9/2005 | Friedman et al. | |
| 2005/0288730 A1 | 12/2005 | Deem et al. | |
| 2006/0009759 A1 | 1/2006 | Christian et al. | |
| 2006/0093673 A1 | 5/2006 | Coury et al. | |
| 2006/0135536 A9 | 6/2006 | Fedida et al. | |
| 2007/0055184 A1 | 3/2007 | Echt et al. | |
| 2007/0083193 A1 | 4/2007 | Werneth et al. | |
| 2007/0118183 A1 | 5/2007 | Gelfand et al. | |
| 2007/0156185 A1 | 7/2007 | Swanson et al. | |
| 2007/0179543 A1 | 8/2007 | Ben-David et al. | |
| 2007/0213771 A1 | 9/2007 | Spinner et al. | |
| 2007/0265687 A1 | 11/2007 | Deem et al. | |
| 2008/0004662 A1 | 1/2008 | Peters et al. | |
| 2008/0294229 A1 | 11/2008 | Friedman et al. | |
| 2008/0300571 A1 | 12/2008 | Lepivert | |
| 2008/0312715 A1 | 12/2008 | Asirvatham et al. | |
| 2009/0024017 A1 | 1/2009 | Ruffini et al. | |
| 2009/0076501 A1 | 3/2009 | Bertolero et al. | |
| 2009/0187187 A1 | 7/2009 | Asirvatham et al. | |
| 2010/0106205 A1 | 4/2010 | Silverstone | |
| 2013/0012938 A1 | 1/2013 | Koestner | |
| 2016/0051322 A1 | 2/2016 | Asirvatham et al. | |
| 2016/0287329 A1 | 10/2016 | Asirvatham et al. | |

FOREIGN PATENT DOCUMENTS

| | | |
|---|---|---|
| WO | WO2010022275 | 2/2010 |
| WO | WO2011075328 | 6/2011 |

OTHER PUBLICATIONS

Boyd et al., "Differential recovery of regional atrial contraction after restoration of sinus rhythm after intraoperative linear radiofrequency ablation for atrial fibrillation," Am J Cardiol., 103(4):528-534, Epub Dec. 25, 2008.

Coyne et al., "Assessing the direct costs of treating nonvalvular atrial fibrillation in the United States," Value Health, 9(5):348-356, Sep.-Oct. 2006.

Go et al., "Prevalence of diagnosed atrial fibrillation in adults: national implications for rhythm management and stroke prevention: the AnTicoagulation and Risk Factors in Atrial Fibrillation (ATRIA) Study," JAMA, 285(18):2370-2375, May 9, 2001.

International Preliminary Report on Patentability for PCT/US2010/058950 dated Jun. 19, 2012, 14 pages.

International Search Report and Written Opinion for PCT/US2010/058950 dated Jan. 28, 2011, 19 pages.

Katritsis et al., "Rapid pulmonary vein isolation combined with autonomic ganglia modification: a randomized study," Heart Rhythm., 8(5):672-678, Epub Dec. 31, 2010.

Lemery et al., "Feasibility study of endocardial mapping of ganglionated plexuses during catheter ablation of atrial fibrillation," Heart Rhythm., 3(4):387-396, Epub Feb. 28, 2006.

Madhavan et al., "Percutaneous epicardial ablation of cardiac ganglionated plexi without myocardial injury in the canine: A novel treatment strategy for atrial fibrillation," Heart Rhythm, 9(5)Suppl. 1, pp. S331-S332, May 2012.

Madhavan et al., "Percutaneous epicardial ablation of cardiac ganglionated plexi without myocardial injury in the canine: a novel treatment strategy for atrial fibrillation," Poster presented at Heart Rhythm Society, May 11, 2012, 1 page.

Madhavan et al., "PO04-105—Percutaneous epicardial ablation of cardiac ganglionated plexi without myocardial injury in the canine: a novel treatment strategy for atrial fibrillation," Heart Rhythm Society, May 11, 2012, 1 page [abstract].

McClelland et al., "Preliminary results of a limited thoracotomy: new approach to treat atrial fibrillation," J Cardiovasc Electrophysiol., 18(12):1289-1295, Epub Oct. 5, 2007.

Mehall et al., "Intraoperative epicardial electrophysiologic mapping and isolation of autonomic ganglionic plexi," Ann Thorac Surg., 83(2):538-541, Feb. 2007.

Miyasaka et al., "Secular trends in incidence of atrial fibrillation in Olmsted County, Minnesota, 1980 to 2000, and implications on the projections for future prevalence," Circulation, 114(2):119-125, Epub Jul. 3, 2006.

Myerburg et al., "Interpretation of outcomes of antiarrhythmic clinical trials: design features and population impact," Circulation, 97(15):1514-1521, Apr. 21, 1998.

Ohkubo et al., "Combined effect of pulmonary vein isolation and ablation of cardiac autonomic nerves for atrial fibrillation," Int Heart J., 49(6):661-670, Nov. 2008.

(56) References Cited

OTHER PUBLICATIONS

Pokushalov et al., "Ganglionated plexi ablation for longstanding persistent atrial fibrillation," Europace, 12(3):342-346, Mar. 2010.
Pokushalov et al., "Left atrial ablation at the anatomic areas of ganglionated plexi for paroxysmal atrial fibrillation," Pacing Clin Electrophysiol., 33(10):1231-1238, Oct. 2010.
Swerdlow et al., "Advanced ICD troubleshooting: Part I," Pacing Clin Electrophysiol., 28(12):1322-1346, Dec. 2005.
Weerasooriya et al., "Catheter ablation for atrial fibrillation: are results maintained at 5 years of follow-up?" J Am Coll Cardiol., 57(2):160-166, Jan. 11, 2011.

* cited by examiner

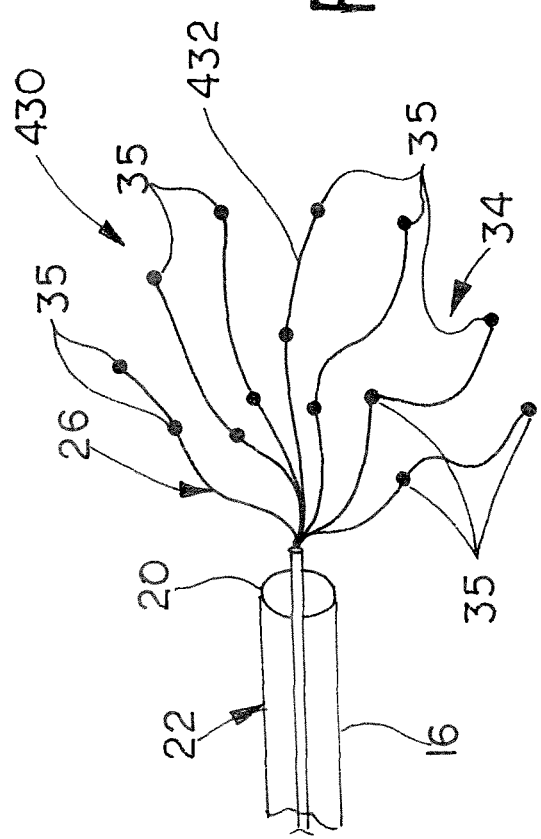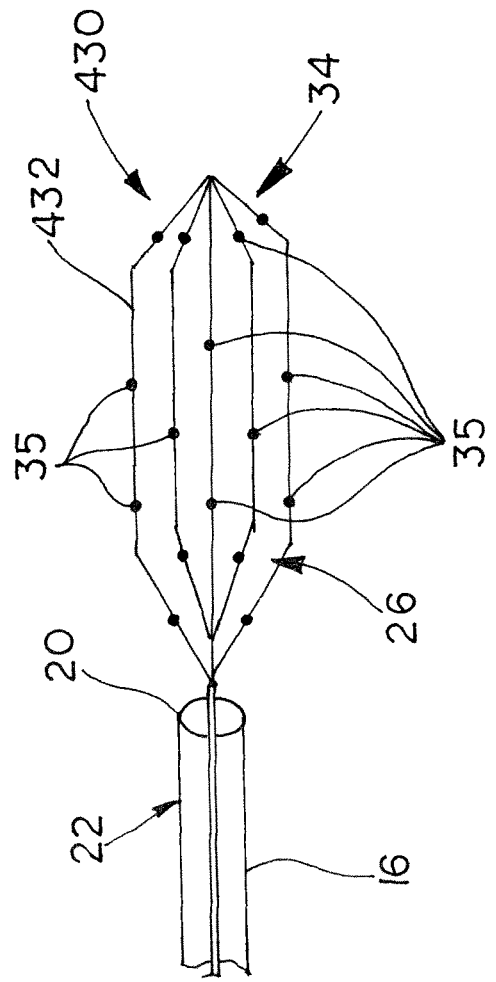

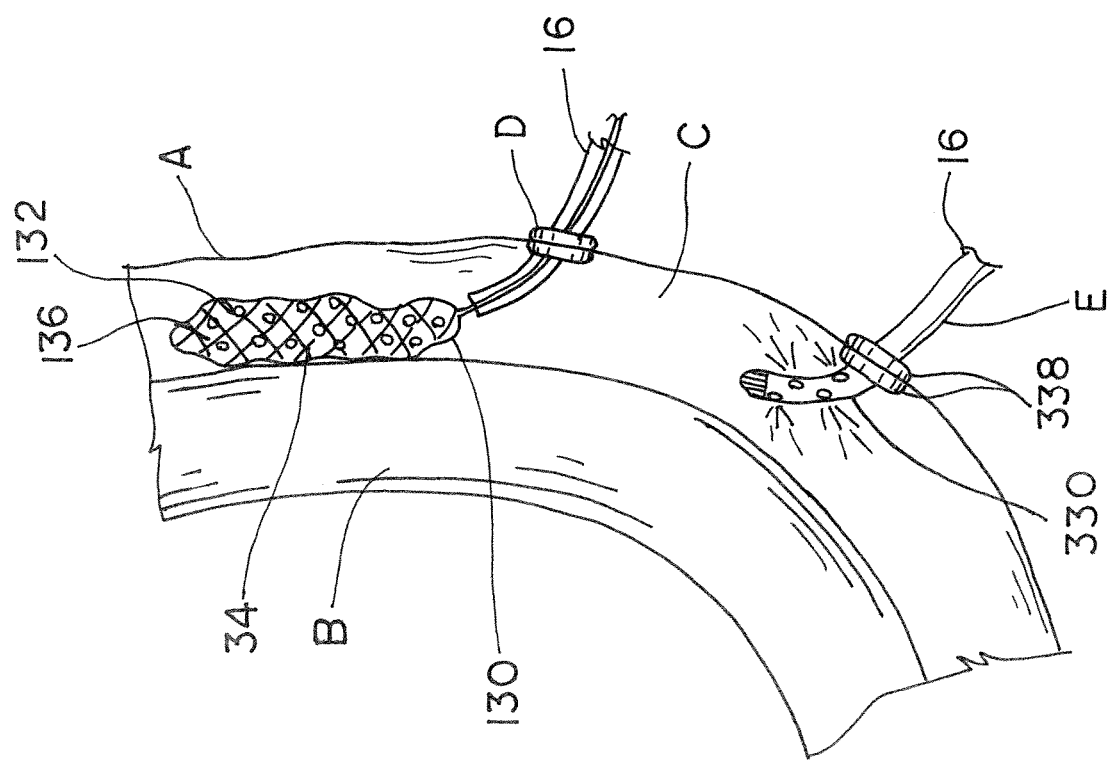

DEVICE AND METHOD FOR TREATING CARDIAC DISORDERS BY MODULATING AUTONOMIC RESPONSE

FIELD OF THE INVENTION

The present invention relates generally to the treatment of cardiac disorders by recognizing, approximating and/or locating autonomic structures in or around the heart, such as on the surface of the heart or within the pericardial space, and treating or manipulating these autonomic structures with, for example, one or more of stimulation, blocking, ablation, or denervation.

BACKGROUND

The heart is surrounded by an autonomic nervous system (ANS) network. It is well accepted that the autonomic nervous system network creates autonomic responses in the heart. Generally speaking, a variety of nervous tissues such as nerves, ganglia, etc., are disposed on the surface of the heart, in the epicardium or myocardium of the heart, on the pericardial sac surrounding the heart sac, within, upon or beneath the pericardial sac.

This network of nervous tissue includes a variety of nerves and tissue, including the neurons, axons, dendrites, plexi, ganglia and ganglia bundles. In neurological contexts ganglia/ganglion are composed mainly of somata and dendritic structures which are bundled or connected together. Ganglia often interconnect with other ganglia to form a complex system of ganglia known as a plexus. Ganglia provide relay points and intermediary connections between different neurological structures in the body, such as the peripheral and central nervous systems.

Autonomic ganglia, which may be referred to as part of the autonomic nervous system, are those ganglia that contain the cell bodies of autonomic nerves. The autonomic nervous system (ANS or visceral nervous system) is the part of the peripheral nervous system that acts as a control system functioning largely below the level of consciousness, and controls visceral functions. The ANS affects, for example, heart rate, digestion, respiration rate, salivation, perspiration, the diameter of the pupils, micturition (urination), and sexual arousal. Whereas most of the actions of the ANS are involuntary, some actions, such as breathing, work in tandem with the conscious mind. The ANS is classically divided into three subsystems: the enteric nervous system, the parasympathetic nervous system and the sympathetic nervous system. Relatively recently, an important subsystem of autonomic neurones that have been named 'non-adrenergic and non-cholinergic' neurones (because they use nitric oxide as a neurotransmitter) have been described and found to be integral in autonomic function, particularly in the gut and the lungs. With regard to function, the ANS is usually divided into sensory (afferent) and motor (efferent) subsystems. Within these systems, however, there are inhibitory and excitatory synapses between neurones.

Other forms of ganglia include cardiac ganglia. Exemplary forms of cardiac ganglia include, for example, retro-atrial ganglion, interarterial ganglia, aortocaval ganglia, and ganglia around the Oblique Sinus of the heart. These latter ganglion include, for example, the left superior ganglia, the left inferior ganglia, the right superior ganglia, and the right inferior ganglia. There are additional ganglia around the Transverse Sinus of the heart.

Those of skill in the art will realize that still other neural and ganglia structures exist. A more complete discussion of ganglia structures and their topography can be found in Topography of Cardiac Ganglia in the adult Human Heart.

SUMMARY

In accordance with one aspect of the invention, a method of modulating the autonomic nervous system adjacent a pericardial space to treat cardiac disorders comprises the steps of providing a source of a treatment medium, the treatment medium effective to, for example, modulate and/or ablate autonomic nervous system activity, providing an apparatus, for example a catheter, having a proximal end and a distal end, the distal end sized for insertion into the pericardial space at an entry point, providing a delivery assembly for delivery of the treatment medium, the delivery assembly having a proximal end and a distal end, the distal end arranged to be positioned by the distal end of the catheter, providing the distal end of the delivery assembly with a delivery tip, which may include a mapping array, the delivery tip operatively coupled to the source, the delivery tip or the delivery assembly arranged to position the delivery assembly or tip and to perform a modulation step to deliver the treatment medium to a selected location, and/or the mapping array may be arranged to sense a level of autonomic nervous system activity within the pericardial space and to create an output, using the output to position the delivery tip at a selected treatment location within the pericardial space, and performing a modulation step by supplying the treatment medium to the selected location via the delivery tip.

In accordance with one or more preferred forms, the method may include providing the delivery tip of the medium delivery assembly with a plurality of delivery points, and using the plurality of delivery points to disperse the treatment medium at a plurality of treatment areas within the pericardial space. Further, delivery tip of the medium delivery may be provided with a dispersion means having an exposed area, which may be used to disperse the treatment medium over a treatment area, the treatment area greater than the exposed area. Additional preferred steps may include using the mapping array after the modulation step to sense a follow-up level of autonomic nervous system activity at the selected location, and comparing the follow-up level of autonomic nervous system activity to a threshold. One may determine, directly or indirectly, whether the follow-up level of autonomic nervous system activity is above a threshold, and then perform a subsequent modulation step.

The preferred method may include providing a monitor arranged to create an output, periodically using the mapping array after the modulation step to sense a follow-up level of autonomic nervous system activity at the selected location and providing a subsequent output to the monitor, comparing the subsequent output to the threshold level of autonomic nervous system activity, and determining whether an additional modulation step is desired. It is also contemplated to use the mapping array or other suitable mapping means after the modulation step to sense a follow-up level of autonomic nervous system activity at the selected location and provide a subsequent output to the monitor, compare the subsequent output to the threshold level of autonomic nervous system activity, determining whether an ablation step is desired, and perform the ablation step by supplying the treatment medium to the selected location via the delivery tip. The method contemplates determining an amount of the treatment medium effective to perform the modulation and/or ablation step, determining a desired duration for the modulation step, and performing the modulation step for the desired duration. The mapping means or mapping array may be operatively coupled to an external system such as, for example, an ECG system, to determine effectiveness.

In accordance with an exemplary aspect, the system may use dynamic modulation with on-line monitoring for autonomic effects. This includes a specific algorithm involving pacing from one or more poles of the array or separate catheters at high and low rate timed so as not to capture atrial myocardium. Analysis of the retrieved signals compared prior to and after intervention will allow detection of whether the desired result on autonomic modulation has been achieved. Specifically, it will be possible to monitor one or more of changes in blood pressure, heart rate, atrioventricular nodal conduction, atrial myocardial refractory period, and heart rate variation along with the frequency and occurrence of the specific detected electrograms in and around the cardiac ganglia.

In accordance with further preferred aspects, the method includes using the mapping array after the modulation step to sense a follow-up level of autonomic nervous system activity at the selected location, comparing the follow-up level of autonomic nervous system activity to a threshold, and performing a subsequent permanent modulation step. Additional preferred steps include providing the delivery tip with an expandable portion shiftable between a collapsed state and an expanded state, coupling the delivery tip to the expandable portion, and expanding the expandable portion after placement of the delivery tip at the location within the pericardial space. Further steps include selecting the treatment medium as one of electrical energy, a pharmaceutical composition, a chemical composition, an exothermic agent, an endothermic agent, or vibration.

In accordance with a yet further aspect of the invention, a method of modulating the autonomic nervous system adjacent a pericardial space to treat cardiac disorders comprises the steps of providing a catheter having a proximal end and a distal end, the distal end sized for insertion into the pericardial space, providing a delivery assembly, the delivery assembly having a proximal end and a distal end, the distal end arranged to be positioned by the distal end of the catheter, providing the distal end of the delivery assembly with a delivery tip, and providing the delivery tip with an electrode array, positioning to the catheter to place the delivery tip at a location in the pericardial space, using the electrode array to take a first indication of autonomic nervous system activity at the location, using the electrode array to apply electrical energy at the location, using the electrode array to take a second indication of autonomic nervous system activity at the location, and comparing the first indication and the second indication to determine whether the autonomic nervous system activity has been modulated at the location. The electrical energy may take one of a number of possible forms.

In accordance with additional preferred forms, the method may include providing the delivery tip with an expandable portion shiftable between a collapsed state and an expanded state, positioning the electrode array on or within the expandable portion, expanding the expandable portion after placement of the delivery tip at the location within the pericardial space. Further, the method may include forming the expandable portion from an expandable metal material, securing the expandable portion in the collapsed state using a sheath, and shifting the expandable portion to the deployed state by removing the sheath after placing the expandable portion at the location. An expansion balloon may be coupled to an expansion medium, and the balloon may be shifted to the deployed state by communicating the expansion medium to the balloon after placing the balloon at the location. Further, an expandable porous medium may be coupled to an expansion delivery means and the medium may be shifted to the expanded state by communicating the expansion agent or energy to the medium after placing the active area at the location and urging the treatment means into close contact with the area to be treated.

Further preferred steps include providing a processor operable to execute a filtering algorithm, providing an electrical coupling between the electrode array and the processor, communicating the first indication to the processor as a first input and the second indication to the processor as a second input, using the filtering algorithm to generate to an output indicative of the first indication or the second indication, and comparing the output to a threshold level of autonomic nervous system activity.

In accordance with yet another aspect of the invention, a method for modulating the autonomic nervous system adjacent a pericardial space to treat cardiac disorders comprises the steps of providing a catheter having a proximal end, and a distal end, the distal end sized for insertion into the pericardial space, providing a treatment source arranged to supply a treatment medium, providing a medium delivery assembly, the medium delivery assembly having a proximal end and a distal end and sized to extend through the lumen of the catheter, providing the distal end of the delivery assembly with a delivery tip arranged to extend from the distal end of the catheter and into the pericardial space, providing the delivery tip with a plurality of electrodes, providing a connector operatively coupling the delivery tip of the medium delivery assembly to the treatment source, and providing the delivery tip of the medium delivery assembly with a plurality of delivery points for delivering the treatment medium at a plurality of treatment areas within the pericardial space.

In accordance with yet an additional aspect of the invention, a method for modulating the autonomic nervous system adjacent a pericardial space to treat cardiac disorders comprises providing a catheter having a proximal end, and a distal end, the distal end sized for insertion into the pericardial space, providing a source of electrical energy, providing a delivery assembly, the medium delivery assembly having a proximal end and a distal end, the distal end arranged to be positioned by the distal end of the catheter, providing the distal end of the delivery assembly with a delivery tip comprising a plurality of electrodes sized for placement in the pericardial space, the plurality of electrodes operatively coupled to the source and forming a plurality of delivery points for delivering the electrical energy from the source to a plurality of treatment areas within the pericardial space, selecting a treatment location within the pericardial space, performing a modulation step by applying electrical energy form the source to the treatment location via the delivery tip.

In accordance with a further exemplary aspect, the system may include a device that allows pericardial manipulation without "leakage" of instilled material into the extra pericardial space. Specifically, two containing components are created, which may take the form of phalanges or wings on the sheath placed into the pericardial space, and these components may be formed of a finely enmeshed Nitinol. The components expand on either side of the pericardium at the site of entry. These can then be manually approximated so as to create as new. This iteration of the sheath may be particularly compatible with modulation options described below where direct current energy is accomplished via a virtual electrode created by instilled pericardial saline and for installation of alcohol or other ganliolytic agents.

In accordance with another aspect, a method for modulating the autonomic nervous system adjacent a pericardial space to treat cardiac disorders comprises providing a catheter having a proximal end and a distal end, the distal end sized for insertion into the pericardial space, providing a delivery assembly, the medium delivery assembly having a proximal end and a distal end, the distal end arranged to be positioned by the distal end of the catheter, providing the distal end of the delivery assembly with a delivery tip sized for placement in the pericardial space, the delivery tip comprising a movable component arranged to apply energy, for example kinetic, mechanical or other suitable energy, to a treatment location within the pericardial space adjacent the delivery tip, providing a mapping array comprising a plurality of electrodes positionable within the pericardial space, the mapping array to sense a level of autonomic nervous system activity within the pericardial space and to create an output, using the output to position the delivery tip at the treatment location within the pericardial space, performing a modulation step by activating the movable component.

In further accordance with one or more of the exemplary forms discussed herein, exemplary methods of treating may include performing modulations/interventions of varying durations. By varying the duration, it is possible to achieve varying effects on the targeted treatment area. For example, the effect of a modulation may be temporary and/or reversible, or the effect of a modulation step may be irreversible in the form of a permanent ablation or inactivation of the targeted nervous tissue. Additionally, variations in duration may be selected based on whether the condition is acute, sub-acute, or chronic. For example, for treatment of an acute condition, the method may consist of modulation over a relatively short term measured in, for example, minutes or hours. Once again, this modulation may be performed electrically, mechanically, chemically, or using thermal approaches. For treatment of a sub-acute condition, the treatment may be performed over an intermediate term which may be measured, for example in days. One exemplary treatment for sub-acute conditions may involve the placement of a fluid retention element filled with, or in flow communication with, a treatment source consisting of, for example, alcohol, procainamide, beta blockers, or other suitable agents. These agents may be placed in the pericardial space for a period of days, and using the sensing functions discussed herein, or other suitable sensing functions, the level of autonomic nervous system activity may be periodically assessed over a selected time frame. During the ensuing time period, adjustment of the modulation step or permanent ablation may be performed. In the face of chronic conditions, the treatment may be performed over a relatively long time which may be measured, for example, in weeks, months or years of treatment. Treatment of chronic conditions may include placing implantable devices to deliver treatment in the form of electrical energy, mechanical cutting or vibration, chemical agents, or thermal therapy. These exemplary therapies can be delivered continuously, or the device can reside in place and can receive inputs from a sensing component that monitors the heart to detect a disorder that requires therapy. The system can then deliver therapy when additional therapy is desired.

In further accordance with one or more of the exemplary methods discussed herein, treatment may be implemented or selected to have varying effects on the autonomic nervous system. The disclosed system and methods may modulate the targeted treatment area without permanently affecting that target, such as by electrical stimulation or blocking of autonomic nerve signals, without damaging the nerve. Alternatively, a targeted area may be permanently modulated by, for example, thermal, chemical, electrical, or mechanical ablation/destruction of a nerve or ganglia.

Using the exemplary system and methods described herein, treatment of a number of cardiac disorders, as well as autonomic disorders related to cardiac function, can be treated by modulating autonomic response. For example, the disclosed system and method may be used to treat cardiac arrhythmias such as atrial fibrillation, ventricular fibrillation, atrial or supra-ventricular ventricular tachycardias, neurocardiogenic syncope, inappropriate sinus tachycardia, and postural orthostatic tachycardia syndrome. Additional conditions that can be treated include forms of heart failure such as, for example, diastolic dysfunction and cardiomyopathy, as well as one or more sources of pain such as cardiac and non-cardiac related chest pain.

It may be desirable to target these autonomic responses via ANS modulation as a means or method of treating a variety of cardiac disorders, such as, for example, cardiac arrythmias. In general, in at least some forms of treatment it may be desirable to modulate the autonomic nervous system, and to do so without causing damage to other tissues of the heart, such as the myocardium and/or surrounding tissues and blood vessels. As disclosed herein, modulating the target means affecting the normal/natural function of the targeted area in a way that changes the physiology or physiologic activity of the system. The means of modulation includes electrical, chemical, thermal, or mechanical modulation and/or ablation. In electrical modulation, electrical energy is sent or otherwise applied to the targeted are of the ANS and sends or disrupts signals along the ANS tissue. Using direct current (DC) or alternating current (AC), one may temporarily or permanently disrupt signals along the nervous tissue.

Mechanical means may include vibrational energy to send of disrupt signals along nervous tissue, or physically severing or otherwise disrupting nervous tissue, while chemical means may include the use of agents that destroy nervous tissue to disrupt signals along nervous tissue (e.g. ethanol, phenol, etc), or use of drugs that temporarily disrupt signals along nervous tissue (e.g. procainamide, lidocaine), or agents to induce signals along nervous tissue. Finally, thermal may include the use of Radio Frequency energy to temporarily or permanently disrupt signals along nervous tissue, or use of cryogenic energy (cooling) to temporarily or permanently disrupt signals along nervous tissue.

BRIEF DESCRIPTION OF THE DRAWINGS

FIG. 9 is an enlarged fragmentary elevational view of still another exemplary form of an expandable treatment delivery tip having an electrode array and shown in an expanded or deployed state.

FIG. 10 is an enlarged fragmentary elevational view of yet a further exemplary form of an expandable treatment delivery tip having an expandable electrode array and shown in an expanded or deployed state.

FIG. 11 is an enlarged fragmentary cross-sectional view of a heart illustrating the treatment delivery tip of FIGS. 2 and 3 inserted into the pericardial space between the pericardium and the myocardium at a first location, and further illustrating the treatment delivery tip of FIGS. 6-8 inserted into the current pericardial space at a second location.

DETAILED DESCRIPTION OF THE PREFERRED EMBODIMENTS

Although the following text sets forth a detailed description of an exemplary embodiment of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Based upon reading this disclosure, those of skill in the act may be able to implement one or more alternative embodiments, using either current technology or technology developed after the filing date of this patent. Such additional indictments would still fall within the scope of the claims defining the invention.

Figure 1:
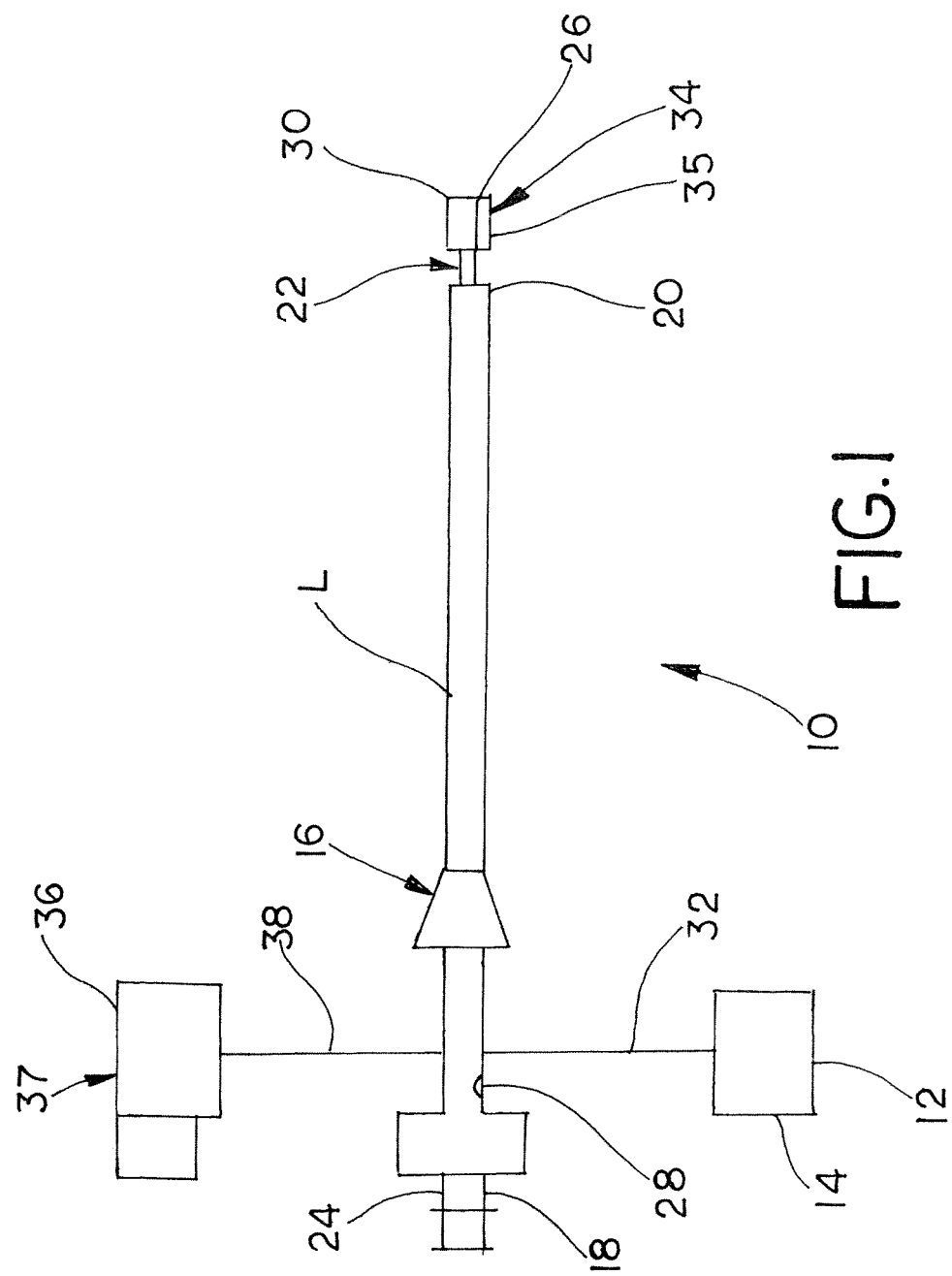
FIG. 1 schematic view of a device for modulating the autonomic nervous system adjacent a pericardial space to treat cardiac arrhythmia and/or other cardiac disorders and assembled in accordance with the teachings of a disclosed example of the present invention.

Referring now to the drawings FIG. 1 illustrates a device 10 for modulating the autonomic nervous system assembled in accordance with the teachings of a disclosed example of the present invention. The device 10 includes a treatment source 12 arranged to supply a treatment medium 14. The treatment medium 14 as illustrated only schematically in FIG. 1, and certain exemplary forms for the treatment medium 14 will be discussed in greater detail below. A catheter 16 is shown and includes a proximal end 18 and a distal end 20, with the distal end 20 sized for insertion into a pericardial space. A variety of conventional catheters available may prove suitable. The pericardial space is not shown in FIG. 1, but will be discussed in greater detail below. The device 10 also includes a medium delivery assembly 22 having a proximal end 24 and a distal end 26. The proximal and 24 of the medium delivery assembly 22 may protrude from the proximal end 18 of the catheter 16. Alternatively, the proximal and 24 of the medium delivery assembly 22 may be concealed within the catheter 16 and accessible via, for example, a suitable access port 28. Those of skill in the art will appreciate that the catheter 16 may be used to position the distal and 20 of the catheter a selected location within the pericardial space, such that the distal end 26 of the medium delivery assembly 22 may be positioned and the desired location within the pericardial space by the catheter 16. The distal end 26 of the delivery assembly 22 includes a delivery tip 30 arranged to extend away from the distal end 20 of the catheter 16 into, for example, the pericardial space. The delivery tip 30 may take a number of possible forms as will be outlined in greater detail below, and in one or more exemplary forms the delivery tip 30 may include an expandable portion as well as some means or mechanism for dispersing the treatment medium over an area larger than the area of the delivery tip itself, which will be outlined in greater detail below. A connector 32 is provided which operatively couples the delivery tip 30 of the medium delivery assembly 22 to the treatment source 12 and hence to the treatment medium 14. Although only a portion of the connector 32 as shown in FIG. 1, it will be understood that the connector 32 may run through a lumen L of the catheter 16 or, alternatively, may run along the catheter 16. Still further alternatives are possible.

As used herein, it is contemplated that the delivery tip may take a number of possible forms. For example, a portion of the delivery tip may form an anchoring portion, or a separate anchoring component may be employed. For example, the delivery tip may have a curve or bend, and the portion of the delivery tip that delivers the treatment medium may be carried on an inside curve, a lateral curve, or and outside curve of a bend, and the device may use a reversible or irreversible anchor to urge the delivery tip/treatment means against the target or desired area. This may be especially useful in, for example, the oblique sinus. Those of skill in the art, upon reading the present disclosure, will understand that the use of the term "delivery tip" herein would include such situations where the delivery tip includes or is used in conjunction with a separate anchor, and would include situations where the actual treatment delivery means or mechanism is not disposed at the distal-most portion of the delivery assembly.

Depending on the specific form of the treatment medium 14, the connector 32 may take a variety of forms as will be discussed in greater detail below. Consequently, the delivery tip 30 is capable of routing or communicating the treatment medium 14 into the pericardial space in a number of possible manners, with specific exemplary manners to be discussed in greater detail below. The delivery tip 30 of the medium delivery assembly 22 includes a plurality of delivery points for delivering the treatment medium at a treatment area or at a plurality of treatment areas within the pericardial space.

Referring still to FIG. 1, in one or more preferred forms, the device 10 may include an electrode system or array 34. The electrode array 34 may take the form of one or more individual electrodes 35. The electrodes 35 may be, for example, either a single or a plurality of unipolar electrodes with a common return electrode, or may be a single or plurality of bipolar pairs of electrodes which may be contiguous or non-contiguous. The electrode array is shown only schematically in FIG. 1. The electrode array 34 is preferably coupled to a signal monitoring and control system 36 by a suitable link 38 which may extend through the catheter 16, or which alternatively may extend along the catheter 16, or which further may be routed to the desired pericardial space using other conventional means. The signal monitoring and control system 36 preferably is coupled to a processor 40, and the processor 40 may include a memory which may store a filtering algorithm as a set of instructions in a computer readable medium. As will be explained in greater detail below, the electrode array 34 may be used to sense the level of autonomic nervous system activity within the pericardial space and, either alone or in combination with the signal monitoring and control system 36, will generate an output indicative of the level of autonomic nervous system activity sensed by the electrode array 34. Preferably, the electrode array 34, the electrode 35, and the signal monitoring and control system 36 together form a navigation or mapping system 37 to aid the operator in identifying a desired or target treatment area, and in delivering treatment.

Figure 2:
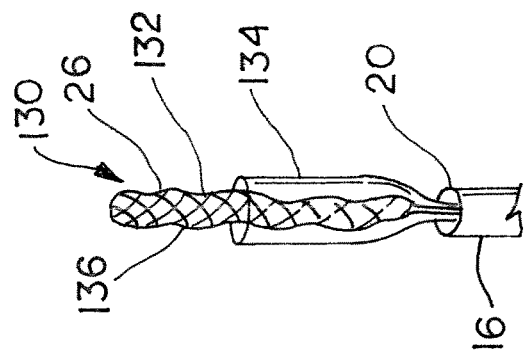
FIG. 2 is an enlarged fragmentary elevational view of one exemplary form of an expandable treatment delivery tip forming the treatment delivery assembly portion of the device of FIG. 1 and shown in a collapsed or undeployed state.
Figure 3:
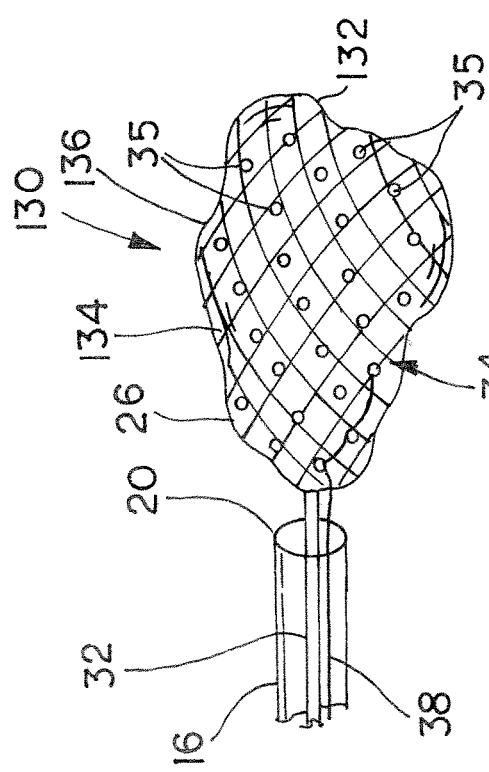
FIG. 3 is another enlarged fragmentary view of the treatment delivery tip of FIG. 2 showing the treatment delivery tip in an expanded or deployed state.

Referring now to FIGS. 2 and 3 of the drawings, an exemplary form of a delivery tip 130 is shown and is assembled in accordance with the teachings of a first disclosed example of the present invention. The delivery tip 130 is attached to or otherwise forms the distal end 26 of the delivery assembly 22 and is shown protruding from the distal end 20 of the catheter 16. The delivery tip 130 includes an expandable end 132 which is shiftable between a collapsed state as shown in FIG. 2 and an expanded state as shown in FIG. 3. A sheath 134 may be provided as shown in FIG. 2 in order to constrain the expandable end 132 in the collapsed state. As shown in FIG. 3, the expandable end 132 may be formed from a number of possible structures including, for example, an expandable balloon, an expandable metal material such as NITINOL, or an expandable porous medium, such as foam. Still further structures may prove suitable. Preferably, the electrode array 34 is carried on the expandable end 132, with the electrode array 34 including a number of individual electrodes 35, all of which are connected to the link 38. The expandable end 132 may also include a fluid retention element 136 such as, for example, a fabric material, a foam, a sponge. Other fluid retention elements may prove suitable. The expandable end 132 is connected to a suitable conduit which in turn is connected to or forms a part of the connector 32 discussed above with respect to FIG. 1. Consequently, by routing the treatment medium 14 from the source 12 into the expandable end 132, the expandable end 132 may be expanded to the expanded or deployed state of FIG. 3. Upon delivery, the expandable end 132 may expand into a given space such as, for example, the pericardial sac, the transverse sinus, the oblique sinus, etc. In accordance with the example disclosed in FIGS. 2 and 3, the electrode array 35 mounted on the expandable element 132 can be used as part of the mapping system 37 for mapping (i.e., to navigate to the desired treatment site, and to determine the orientation of the expandable end 132 at or adjacent to the treatment site). In further accordance with the example disclosed in FIGS. 2 and 3, the electrode array 35 may be used to deliver the treatment medium 14 in the form of energy to a selected treatment site. When energy is selected as the treatment medium 14, the energy may take a variety of forms such as, for example, radiofrequency (RF) energy, direct current (DC) energy, or pulsed electric fields (PEF). Consequently, by delivering energy in any one of the chosen forms, it is possible to modulate nerve signals, such as by blocking nervous system activity, stunning the nervous system activity, or permanently ablating the nervous system activity. In the example of FIG. 3, when a chemical or pharmaceutical agent is selected as the treatment medium 14, the expandable end 132 may be connected via the connector 32 to the treatment source 12 in order to form an infusion system 134 to deliver chemical agents (drugs, alcohol, etc) to the expandable end 132 and hence into the cardiac space. As an alternative, the expandable end 132 may contain or be covered with the fluid retention element 136 to hold the selected treatment medium in a confined area to prevent damage to surrounding tissues. In cross-section, the expandable end 132 may be relatively flat to allow for deployment and positioning in the pericardial space.

Figure 4:
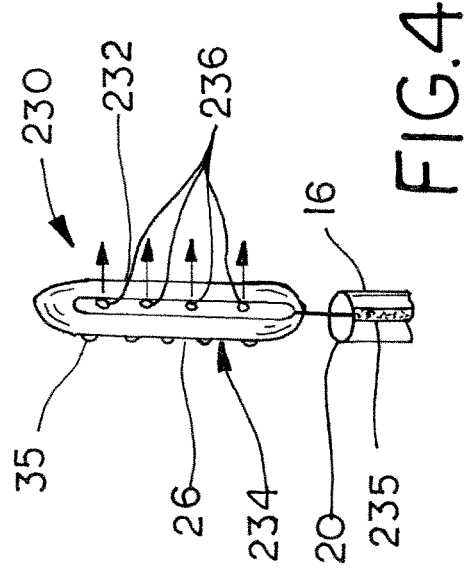
FIG. 4 is an enlarged fragmentary elevational view of another exemplary form of an expandable treatment delivery tip shown in a collapsed or undeployed state.
Figure 5:
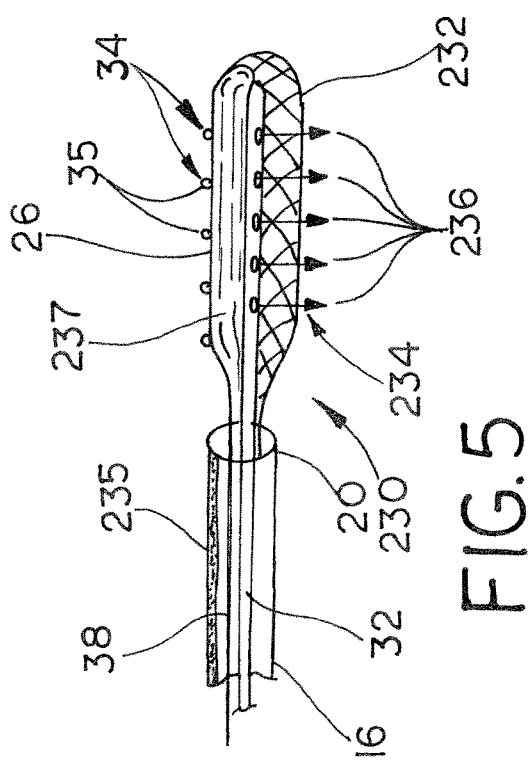
FIG. 5 is another enlarged fragmentary view of the treatment delivery tip of FIG. 5 showing the treatment delivery tip in an expanded or deployed state.

Referring now to FIGS. 4 and 5, another exemplary form of a delivery tip 230 is shown and is assembled in accordance with the teachings of a second disclosed example of the present invention. The delivery tip 230 again is attached to or otherwise forms the distal end 26 of the delivery assembly 22 and is shown protruding from the distal end 20 of the catheter 16. In the example of FIGS. 4 and 5, the expandable end 232 forms a design for facilitating directional deployment of the selected treatment medium 14. Preferably, the electrode array 35 is carried on the expandable end 232, with the electrode array 35 including a number of individual electrodes, all of which are connected to the link 38. As with the example of FIG. 3, when a chemical or pharmaceutical agent is selected as the treatment medium 14, the expandable end 232 may be connected via the connector 32 to the treatment source 12 in order to form an infusion system 234 including a plurality of spaced infusion ports 236 which may function to deliver chemical agents (drugs, alcohol, etc.) to the expandable end 232 and hence into the cardiac space. The expandable end 232 may be expanded in a manner similar to that discussed above with respect to FIGS. 2 and 3, and may, like all the exemplary delivery tips outlined herein, use a sheath to maintain the expandable end in the collapsed state during delivery.

The shaft of the catheter 16 may include or contain differential coatings 235 such as, for example, echogenic coatings, radiopaque coatings, or other coatings, to allow the operator to visualize the orientation of the catheter/delivery tip 230 once it is in position within the desired cardiac space. All other delivery tips outlined herein may also use such coatings as a navigation and deployment aid. The expandable end 232 again preferably includes the electrodes 35, which may be mounted on any surface of the expandable end 232. As with any of the electrodes discussed herein, the electrodes preferably are labeled to allow the operator to know which electrodes are on which side of the expandable element, which serves to facilitate orientation of the device during delivery. Alternatively, the electrodes may be disposed on only a single surface of the delivery tip 230 to allow for differential mapping of tissue to allow for orientation. In accordance with the disclosed example, the ports 236 of the infusion system 234 may be positioned and/or oriented to have directional capabilities, and thus may deliver the treatment medium 14 in line with the orientation of the electrodes/catheter coatings. Further, the expandable end 232 may contain or be covered with a fluid retention element of the type discussed above with respect to FIGS. 2 and 3, and also may contain or be covered by a polymer cover 237 in an orientation which would contain or otherwise prevent the treatment medium 14 being delivered from leaking back towards surrounding tissues.

Figure 8:
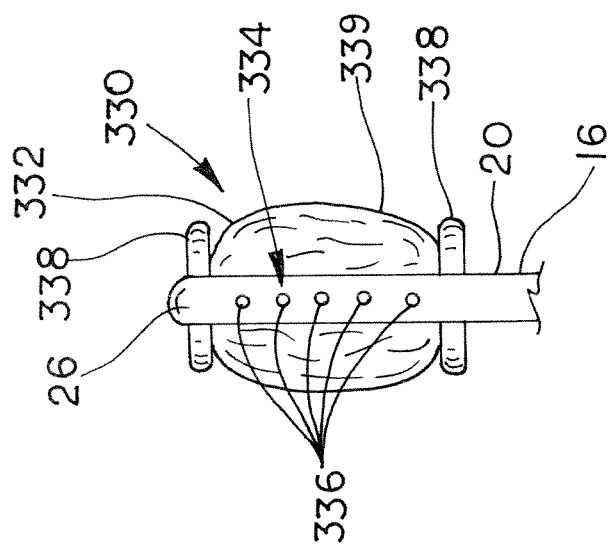
FIG. 8 is an enlarged fragmentary plan view of the treatment delivery tip of FIGS. 6 and 7 showing the treatment delivery tip in an expanded or deployed state from a different perspective.
Figure 6:
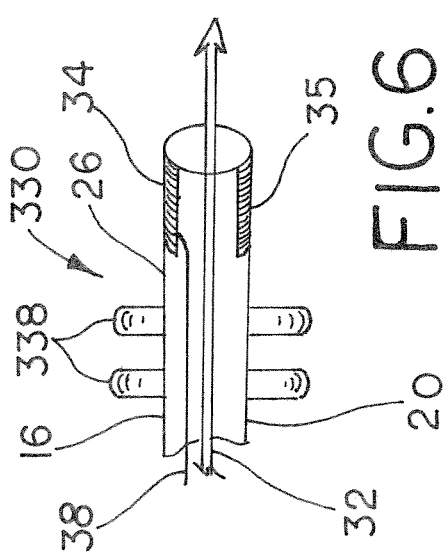
FIG. 6 is an enlarged fragmentary elevational view of still another exemplary form of an expandable treatment delivery tip shown in a collapsed or undeployed state.
Figure 7:
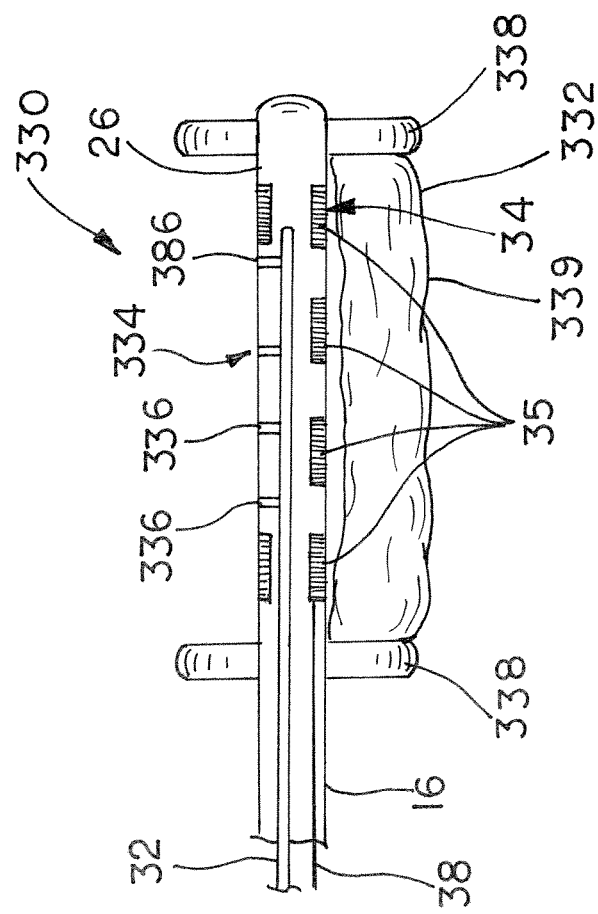
FIG. 7 is another enlarged fragmentary elevational view of the treatment delivery tip of FIG. 6 showing the treatment delivery tip in an expanded or deployed state.

Referring now to FIGS. 6-8, a still further exemplary form of a delivery tip 330 is shown and is assembled in accordance with the teachings of a second disclosed example of the present invention. The delivery tip 330 again is attached to or otherwise forms the distal end 26 of the delivery assembly 22 and is shown protruding from the distal end 20 of the catheter 16. In the example of FIG. 6, the distal end 26 of the delivery assembly forms a conduit for directing the treatment medium 14 in the form of a fluid into the pericardial space. In the example of FIGS. 7 and 8, an expandable end 332 forms a design for facilitating directional deployment of the selected treatment medium 14. Preferably, the electrode array 34 is carried on the expandable end 332, with the electrode array 34 including a number of individual electrodes 35, all of which are connected to the link 38. As with the examples discussed above, when a chemical or pharmaceutical agent is selected as the treatment medium 14, the expandable end 332 may be connected via the connector 32 to the treatment source 12 in order to form an infusion system 334 including a plurality of spaced infusion ports 336 which may function to deliver chemical agents (drugs, alcohol, etc) to the expandable end 332 and hence into the cardiac space. The expandable end 332 may be expanded in a manner similar to that discussed above with respect to the above-described Figures, using any suitable expansion medium. In the example of FIG. 6 and in the example of FIGS. 7 and 8 the delivery tip 330 includes a pair of expandable containing elements 338 which, in accordance with the exemplary form shown, may function to contain a chemical agent within a cardiac space. The containing elements 338 may be formed from a variety of structures or materials, such as an expandable metal such as NITINOL, foam, a balloon, or other structures. The containing elements 338 serve to contain the treatment medium 14 within a selected space and also serve to prevent the treatment medium 14 from migrating or leaking to other areas. The containing elements 338 can be delivered in a collapsed state during catheter positioning and then may be expanded before therapy, and may be constrained with a sheath of desired. As a further alternative, there may be additional containing elements 338 disposed at additional locations along the catheter which can be positioned in any configuration. FIG. 6 shows a version with proximal and distal containing elements 338 disposed proximally of the distally located electrodes. FIG. 7 shows spaced apart proximal and distal containing elements 338, with electrodes 35 and infusion ports 336 disposed between the containing elements 338. Additionally, the example of FIGS. 7 and 8 includes a dorsal containing element 339 which extends between the proximal and distal containing elements 338.

Referring now to FIGS. 9 and 10, another exemplary forms of a delivery tip 430 are shown and are assembled in accordance with the teachings of a further disclosed example of the present invention. The delivery tip 430 again is attached to or otherwise forms the distal end 26 of the delivery assembly 22 and is shown protruding from the distal end 20 of the catheter 16. The delivery tip 430 in each of FIGS. 9 and 10 include expandable ends 432 which carry the electrodes 35. As outlined above, the electrode array 34 and the individual electrodes 35 are coupled to the link 38, and may form a portion of the mapping system 37. If energy is selected as the treatment medium, the electrodes/electrode array also acts to deliver the treatment medium in the form of electrical energy. In each of the example shown, the electrodes 35 are oriented on long wire strands, which may take the form of an expanding fan shape (FIG. 9) or along a more rectilinear frame or array (FIG. 10). In the example of FIG. 9, the strands are constructed of multiple independent wires which can be pushed into the cardiac space and then positioned to deliver energy as the treatment medium. FIG. 10 shows a version with electrodes mounted on an expandable frame which can be placed in the cardiac space. These constructions could also be combined with, for example, the construction of FIGS. 6-8 to concurrently deliver an agent along with the energy.

FIG. 11 illustrates the delivery of two of the above-described embodiments at different locations into the pericardial space. The enlarged fragmentary cross-section of the heart shows the pericardium A, the myocardium B, and the pericardial space C between the pericardium A and the myocardium B. It will be understood that autonomic nervous tissue such as cardiac ganglia will reside in the pericardial space C. The top portion of FIG. 11 shows the delivery tip 130 of FIGS. 2 and 3 delivered into the pericardial space C via an entry point D. The expandable end 132, when expanded, would fill a portion of the pericardial space C. Specifically, the expandable end 132 would expand to extend between the myocardium B and the pericardium A, and also would expand along the pericardial space in a direction perpendicular to the plane of the drawing. Consequently, the electrode array 34 spreads out to occupy a greater space, as does the fluid retention element 136.

Similarly, the bottom portion of FIG. 11 shows a delivery tip which may be the delivery tip 330 of FIG. 6 delivered into the pericardial space C via another entry point E. The containing elements 338 are expanded on opposite sides of the pericardium in order to effectively seal the entry point E. The infusion ports 336 of the infusion system 334 are disposed inside the pericardial space C in order to deliver the treatment medium 14 as a liquid agent. The electrodes 35 of the electrode array 34 are also disposed in the pericardial space C.

Figure 12:
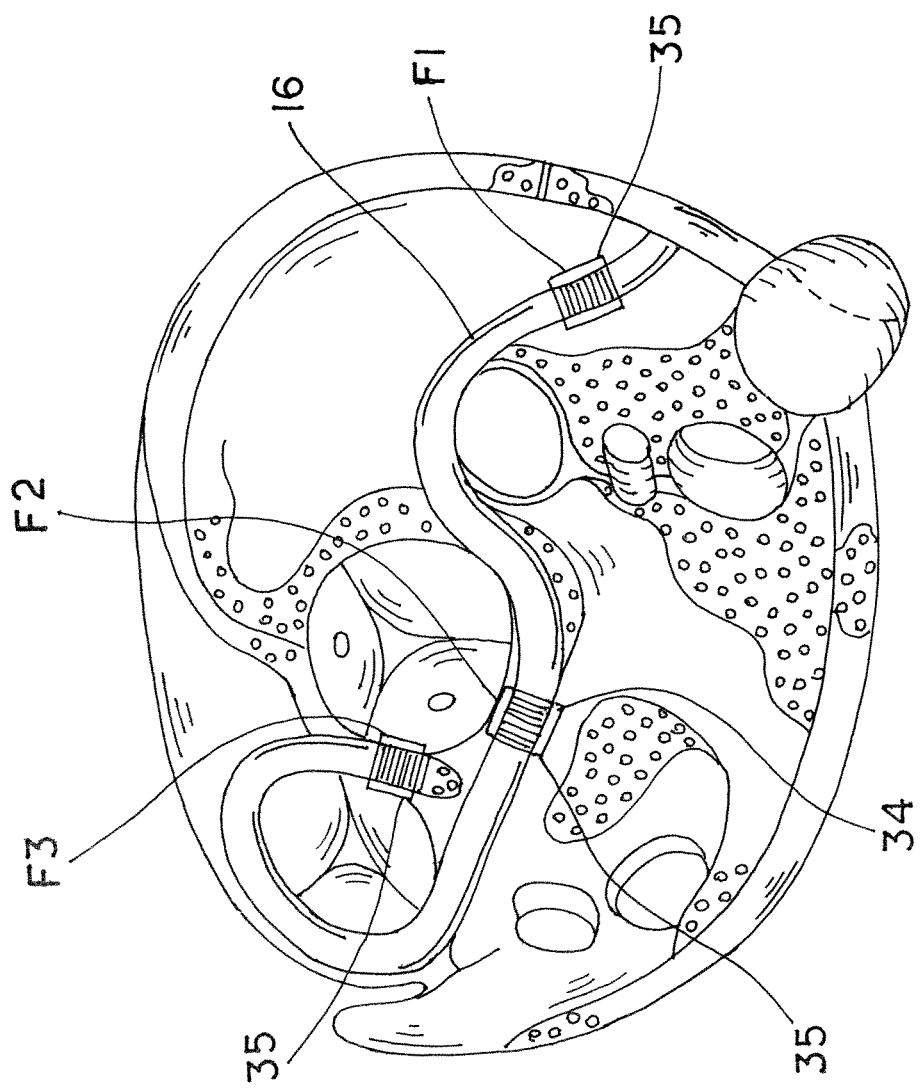
FIG. 12 is an enlarged cross-sectional view of a heart illustrating various ganglionic areas of interest and the delivery of a catheter to various locations along the heart.

FIG. 12 illustrates the delivery of the catheter 16 to various locations along the heart. In the exemplary deployment of FIG. 12, the catheter 16 is positioned along the transverse sinus of the pericardial space and then navigated along the trunks of the superior vena cava, the aorta, and the pulmonary arteries. This exemplary positioning disposes the catheter 16 adjacent multiple clusters of ganglia, each of which can then be modulated by the electrodes 35 of the mapping system 34, and each of which can then be subjected to treatment using any one or more of the exemplary delivery tips described herein to deliver any one of the possible treatment mediums described herein Further, in the example of FIG. 12, the electrodes 35 are positioned at various locations along the catheter labeled F1, F2, and F3. Such a positioning may enable the creation of a bipolar energy delivery field to facilitate broad area coverage at each of the locations F1-F3.

Figure 13:
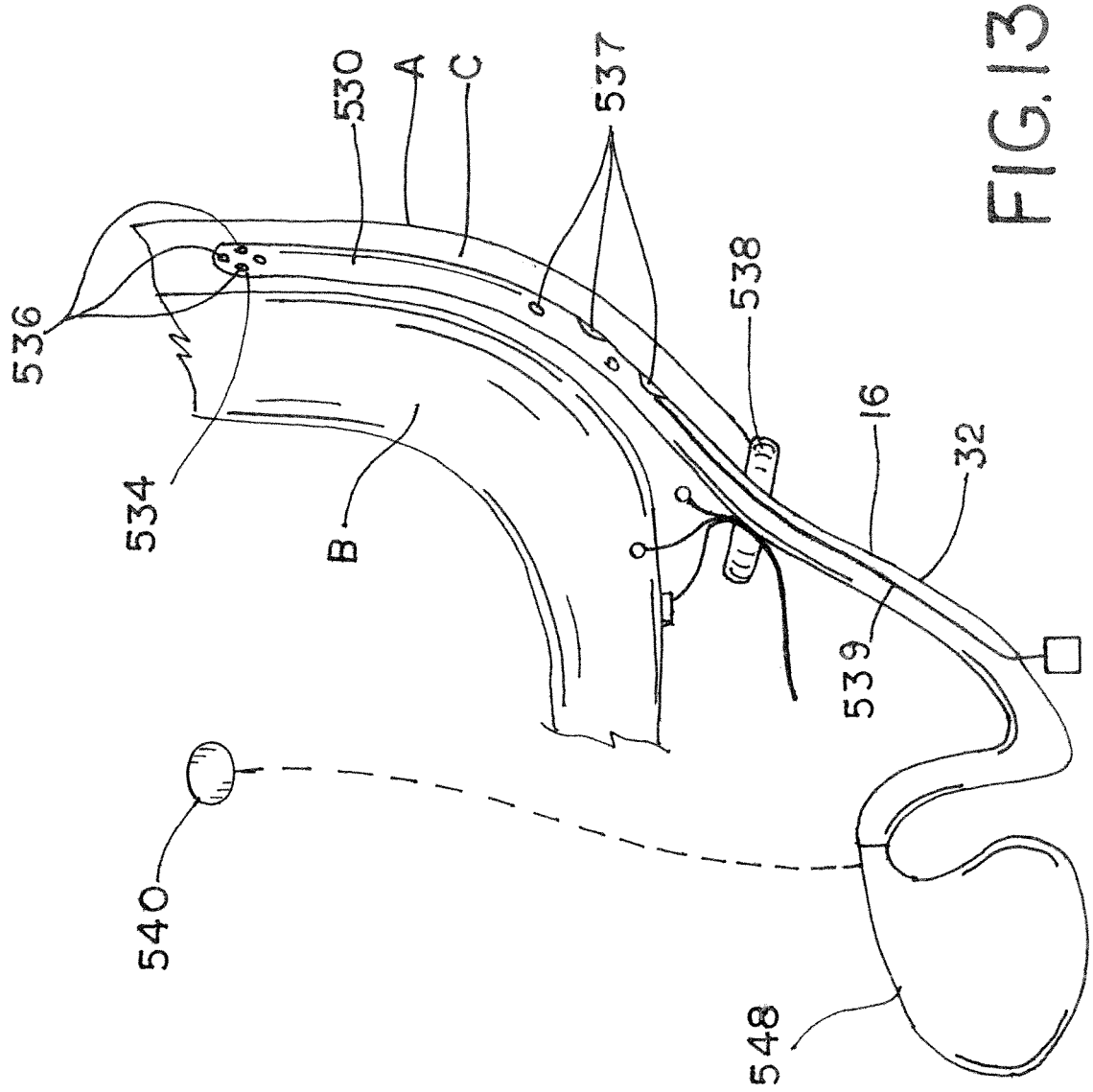
FIG. 13 is another enlarged fragmentary cross-sectional view of a heart illustrating a treatment delivery assembly having infusion ports, suction ports, and a blocking agent disposed in the selected treatment area and coupled to a control unit for the treatment medium comprising a pump and a reservoir.

FIG. 13 shows another exemplary delivery tip 530 assembled in accordance with the teachings of another disclosed example of the present invention. The delivery tip 530 is shown coupled to the treatment source 12 in the form of a reservoir for holding a liquid treatment medium. The delivery tip 530 includes a fluid infusion system 534 having a plurality of spaced apart infusion ports 536 for delivering any one of the selected treatment mediums described herein from the reservoir via the link 32 in the form of a suitable conduit. The delivery tip 530 also includes containing elements 538 to seal the pericardial space C, and further includes a plurality of suction or evacuation ports 537 to selectively withdraw the treatment medium via a suitable return conduit 539. In the example of FIG. 13, the infusion catheter 16 is placed into the pericardial space C and attached to a suitable infusion pump/control system 548 which preferably may be implanted anywhere in the body (e.g. subclavian, subdermal, abdominal cavity, etc.). One or more sensors 540 can be placed along the body of the catheter/delivery tip, in the pericardial space C, on the surface of the heart, within the myocardium, or on the surface of the body. In some preferred forms, communication between the sensors 540 and the control may be accomplished via wireless transmission. The sensors 540 determine if a cardiac event is occurring (arrhythmia, infarction, etc), and then communicate to the pump/control unit to deliver an agent into the pericardial space C via the infusion catheter.

Figure 14:
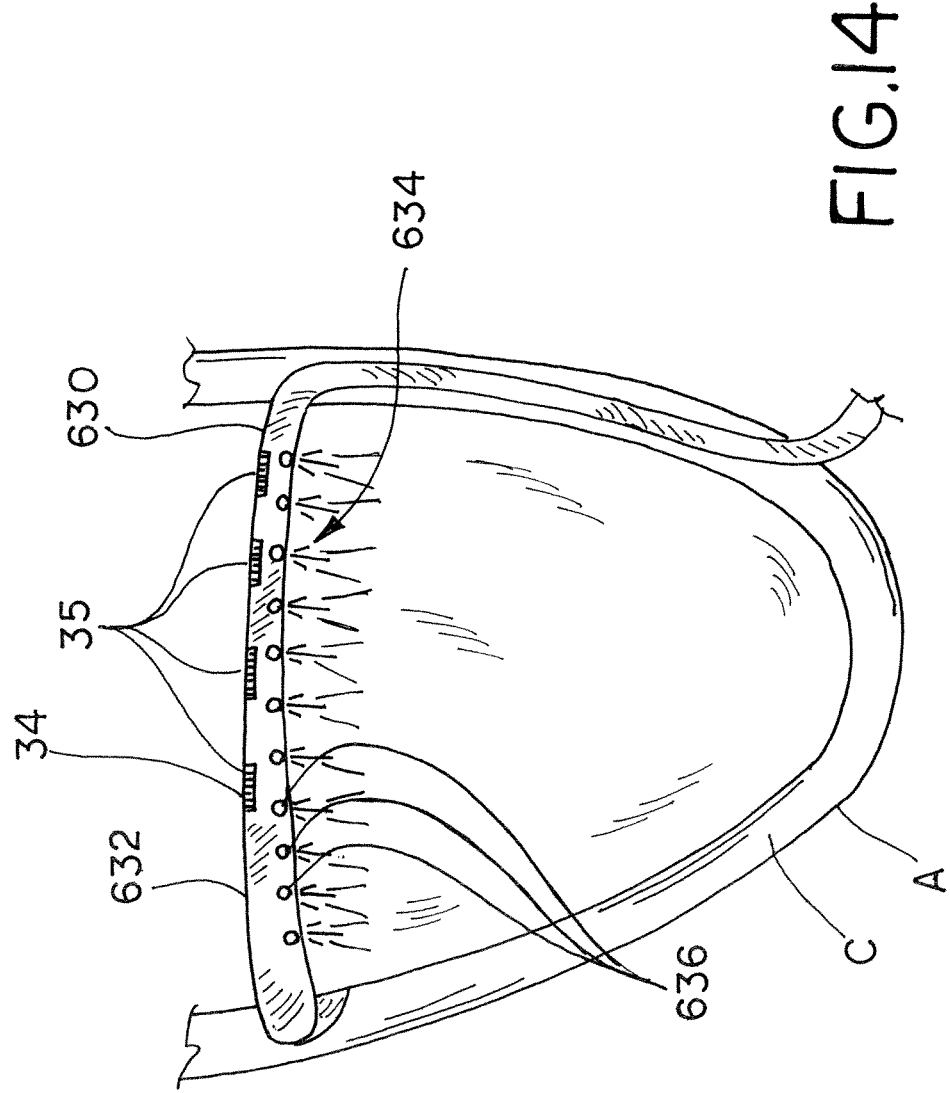
FIG. 14 is yet another enlarged fragmentary cross-sectional view of a heart illustrating another exemplary treatment delivery tip having an electrode array and an infusion system encircling a ventricle of the heart within the pericardial space.

FIG. 14 shows another exemplary form for a delivery tip 630 assembled in accordance with the teachings of an additional disclosed embodiment. In the specific application illustrated, the catheter/delivery system is positioned to modulate nerve tissue along the ventricles of the heart within the pericardial space C. The catheter 16 may be positioned to encircle the epicardial surface of the ventricles, and then may modulate the adjacent nerve tissue. The delivery tip 630 includes a plurality of the electrodes 35 spaced along a length of the tip, and further includes an infusion system 634 having a plurality of spaced apart infusion ports 636. The modulation can be by infusion of an agent and/or delivery of energy via the electrodes 35 along the catheter 16. The catheter can be oriented and aligned such that the infusion ports are positioned to deliver the agent at the top of the ventricles and allow the agent to seep down over the surface of the ventricles.

Figure 15:
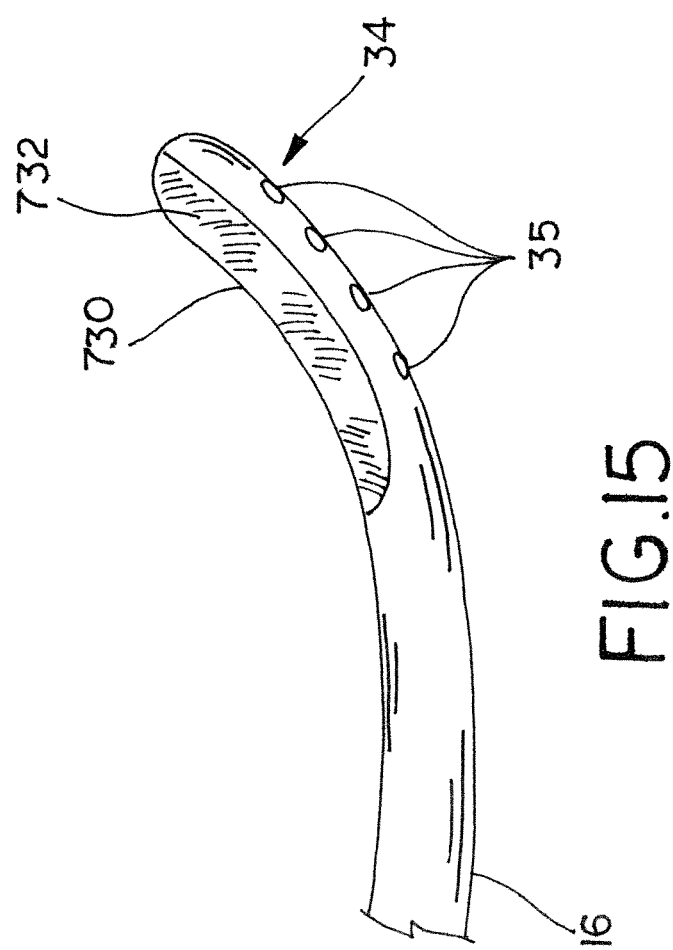
FIG. 15 is an enlarged fragmentary plan view illustrating an exemplary treatment delivery tip having an electrode array and a cryogenic element.

FIGS. 15-18 show several additional delivery tips assembled in accordance with further teachings of the disclosed invention. Each of the examples of FIGS. 15-18 illustrate various forms of a cryogenic delivery tip 730 for delivering thermal energy to selected nerve tissue. FIG. 15 shows the cryogenic delivery tip catheter with a cryogenic element 732 positioned opposite a series of spaced electrodes 35, again for mapping, navigation, and orientation as outlined elsewhere herein, and can be utilized by the operator to orient the catheter 16 with the cryogenic element 732 against myocardium. The delivery tip 730 preferably includes an covering/coating 734 formed of a suitable insulating material. The insulation prevents thermal energy from damaging or affecting other tissues.

Figure 18:
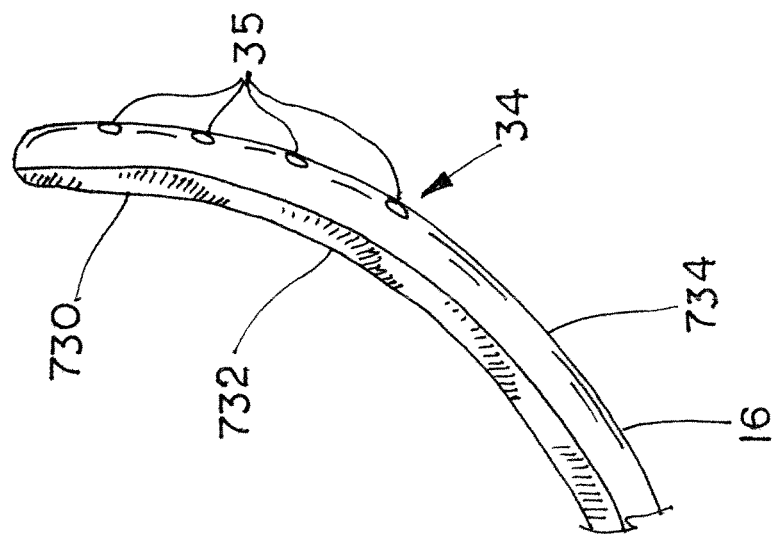
FIG. 18 is another enlarged fragmentary plan view illustrating another exemplary treatment delivery tip having an electrode array, an elongate cryogenic element, and an insulative coating.
Figure 17:
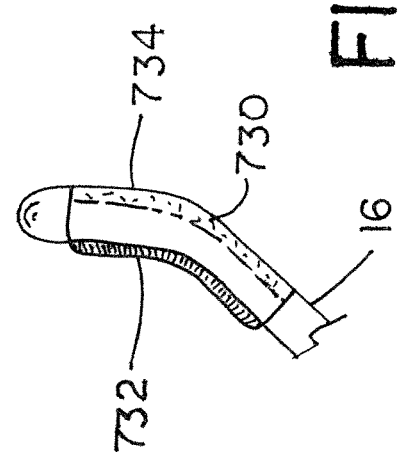
FIG. 17 is another view of the delivery tip of FIG. 16 illustrating thermal insulation applied to the delivery tip.
Figure 16:
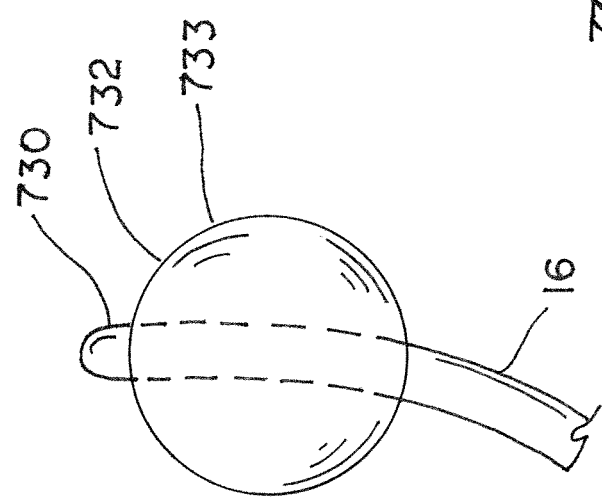
FIG. 16 is another enlarged fragmentary plan view illustrating the exemplary treatment delivery tip having an electrode array and a cryogenic element mounted on an expandable component.

FIG. 16 illustrate a slight variation on the delivery tip 730, as the cryogenic element 732 is carried by an expandable element 733. The expandable element 733 may be made the same as any of the other expandable elements discussed herein, and may be expanded using any of the exemplary expansion mediums discussed herein. In the example shown, the catheter 16 can be delivered with the cryogenic element/expandable element in a collapsed state, and then the expandable element can be expanded to provide broad surface coverage of the cryogenic element over myocardium. The expandable element can have a relatively flat cross-sectional shape to facilitate placement in the pericardial space. Finally, FIG. 18 shows the cryogenic element 732 having an elongated configuration with a corresponding larger elongate surface area. Electrodes 35 are spaced apart along the delivery tip. This version may be particularly useful for cooling the ventricle.

In further accordance with one or more preferred forms of the invention, there may be certain methods and functionalities that may be, depending on the specific form of implementation, common across the various devices and methods discussed herein. For example, it is preferable to implement a system in which it is possible to navigate within the pericardial space to a targeted treatment area, identify the area to be treated, and to assess the effectiveness both during the procedure and after the procedure. These methods may include, for example, ultrasound visualization, electrical-mapping, and filtering of electrical signals detected by, for example, the mapping array discussed herein. Such systems may enable one to visualize and detect ganglia, treat the ganglia, and then assess the status of the ganglia. The status may include whether the has been stunned, killed, or not killed. Such an assessment allows for a sub-acute treatment in which therapy is provided over a course of days, one or more periodic assessments are performed, and then the therapy may be made permanent if the assessment indicates that the therapy has the desired effect. In general, the systems and method outlined herein may allow treatment of the ANS while not affecting the myocardium.

In one or ore of the exemplary devices and methods discussed herein there are a number of exemplary ways to monitor autonomics during therapy, in preparation for therapy, or after therapy. For example, use of the electrodes or electrode array, which may include closely spaced bipole electrodes, coupled with the use of an algorithm to filter out far-field signals of certain frequencies. One possible exemplary algorithm may be based on using the derivative of the electrogram voltage itself. Preferably, the system may be able to pick up the signals while excluding the cardiac myocyte related signals. An additional concept would be to use dynamic recordings; (i.e. an operator could use sub-threshold stimulation or rapid stimulation and then use the effects on the recorded electrograms to better define what the autonomics are). Further, a pressure sensor or a piezoelectric crystal will help detect myocardial contraction when we are stimulating and whichever contraction signal correlates with an electrogram when captured would allow exclusion of that particular electrogram since capturing that leads to muscle capture and thus is likely myocyte generated. Finally, looking at effects on cardiac rhythm or function could also be used; i.e. non-excitatory impulses placed at the site of recording a particular type of signal that would result in noncapture—electrophysiology results (change in refractory period, contractility, inducibility of arrhythmia etc.) would be used to allow deducing that these signals are in fact autonomic nerves.

In accordance with one or more preferred aspects, it may be desirable to specifically identify the signals targeted for manipulation and subsequent modulation. One goal is to identify electrograms arising from the cardiac autonomic system, retroatrial ganglia, and related structures, and distinguish these electrograms from those arising from the atrial, ventricular, and related myocardium.

One aspect of this distinguishing algorithm looks at the frequency of signals. For example, if the frequency of the recorded signal is greater than 50 Hz these are unlikely to be originating from myocardium. However, these signals even when above this frequency cut off are detected may be by themselves misleading since overlapping cardiac structures may be giving rise to the impression of frequently firing myocardial cells. Thus further aspects of this disclosure may clarify when high frequency signals do indeed represent neuronal ganglia or related structure activity.

One of the ways proposed to make this distinction involves template matching of the electrogram morphology. The 50 Hz (or similar value) cut off will apply only if there is a greater than 80% (or similar value) match in morphology of the electrograms being counted for frequency determination. Thus using this refinement of the filtering algorithm overlapping structures which may be detected as rapid firing but will have minimal similarity in electrogram morphology will be excluded.

To further refine the accurate detection of these electrograms involves a dynamic algorithm where rapid stimulation at frequency in two ranges, one where myocardial capture is expected to occur at least intermittently and a second where myocardial capture is unlikely to occur. The recorded electrograms are compared pre and post burst stimulation at the above two frequencies. The disappearance of one set of signals at relatively lower frequencies suggests that those signals were myocardial in origin and the failure for lower frequency stimulation to effect another group of signals which then are decreased or disappear at higher rate stimulation would be diagnostic of a non-cardiac (neuronal) origin for those signals. The now identified myocardial signals are specifically filtered based on their electrogram characteristics and retained in the devices memory. Following the "intervention" (ablation, stimulation, blocking, alcohol, etc., or any of the treatment means outlined herein) are reacquired to assess efficacy of the intervention.

Additional monitoring of autonomics could be accomplished through the use of veratrum alkaloids to monitor for modulation and/or ablation efficacy. Veratrum causes bradycardia and hypotension, and these could be used as endpoints during modulation and/or ablation, whether the ablation or means of ablation is energy-based (RF, AC, DC, etc.) or chemical based (alcohol, etc.), and to determine when treatment has been successful. For example, Veratrum can be given, the modulation/ablation procedure can be started, and then the modulation/ablation is continued until the bradycardia and hypotension is no longer detected.

An alternative agent to use to create the aforementioned endpoints and that can be used as surrogates to monitor for treatment efficacy is Ouabain. Ouabain applied to the epicardial surface (infused into the pericardial space) causes bradycardia and hypotension. Once again, a modulation/ablation procedure (energy based—RF, DC, etc or chemical based—alcohol, etc) can be performed after Ouabain administration and continue until the hypotension and bradycardia disappear.

The identification of ganglia and the navigation to selected ganglia may be accomplished by sensing the ganglia signals, amplifying the ganglia signals, and then filtering out the myocardial electrograms. This may be accomplished in at least one of three exemplary manners. First, a very-low noise amplifier could be used with, for example, a 10 KHz bandwidth. This arrangement could act as a frontend to pick up signals from inside the heart, over the ganglia plexi. A high frequency, high-pass filter could be used in order to minimize the effect of motion and in order to filter out and/or ignore intra-cardiac electrograms (which would saturate the high-gain amplifier).

Second, near-field and far-field signals may be compared. In accordance with this concept, if the near-field signal profile is very similar to the far-field signal profile, then the delivery device is probably disposed in muscle, such as the myocardium. However, if the differences between the near-field signal profile and the far-field signal profile is distinctly different and surpasses a threshold, then the delivery device is probably disposed in nervous tissue, since far-field signal profile will be weighted towards the abundant musculature. Accordingly, it would be desirable to have a narrow-to-wide variable tip recording system. In such an implementation, the closely spaced bipoles would be compared to the more widely spaced bipoles, with morphology/template matching to distinguish nerve from muscle.

Next, a catheter-based imaging system may be employed, which may include thermal spectral imaging, either alone or in combination with electrograms. This may serve to distinguish the autonomics from underlying myocardium. A lower thermal profile with rapid electrograms, even with overlying atrial fibrillation, could help distinguish these structures.

In further accordance with one or more exemplary forms disclosed herein, it may be desirable to use radiopaque and/or echogenic coatings on the catheter in order to assist visualization during the preparation and performance of the treatment procedure. These or other sensing components or methods may be used with treatment of chronic conditions in order to sense, actuate, and treat such conditions. Such sensors may be direct, in which the electrode or electrode array is disposed within the pericardial space, on the myocardium, or on the epicardium. Such sensors also may be indirect, in which the sensor may be worn externally on the skin.

In many applications, it may be desirable to stimulate or block nerve signals using a low current density so as not to capture cardiac muscle. The stimulation may be performed during diastole (when cardiac muscle is not contracting and is not electrically as active).

When performing one or more of the methods outlined herein, it may be desirable to leave the catheter or other device in place in the transverse or oblique sinus. Consequently, there it may be desirable to anchor the catheter and/or the device in place in order to prevent the device from migrating to the ventricle or otherwise migrating out of the desired treatment area. Exemplary forms of anchoring the device may include, for example, mechanical means such as screws, barbs, or balloons, polymers such as clues or gels, or energy means such as RF welding to attachments to tissues such as the epicardial surface of the heart or to the pericardial sac.

Those of skill in the art will understand that the modulation of the cardiac autonomics poses one or more are possible challenges. These potential challenges include recording autonomic activity (for navigation to the autonomics and for feedback of therapeutic efficacy. It is understood that the autonomics may be a number of autonomics which are disposed in number of locations which may be dispersed across a relatively wide area, and which may need to be modulated simultaneously or nearly simultaneously. The autonomic preferably are modulated without damaging, activating, or otherwise affecting the myocardium or other structures such as the aorta, the esophagus, the vagus nerve, etc.

The methods and devices outlined herein may offer a number of general solutions to one or more of the foregoing challenges and concerns. The devices and methods disclosed herein contemplate a number of different means or mechanisms as well as approaches to recording the autonomic activity as discussed above with respect to how to navigate, identify and assess autonomic activity at a selected location. Additionally, the use of chemical and/or pharmaceutical infusion into various spaces in the pericardial sac, such as the oblique sinus, the transverse sinus, the aortocaval sinus, or the entire pericardial space, etc, may enable coverage the very broad area which exceeds the actual area of the inserted device. Further, the use of devices or delivery tips with expandable elements such as expandable metal materials such as NITINOL, a mesh material, an expandable balloon, or other expandable structures, enables the device to carry electrodes and/or agents (via sponges, foam, etc) to a relatively large areas (see, for example, FIGS. 2-10). Finally, the use of modulation in accordance with the teachings discussed herein means that it is possible to affect nervous tissue (autonomics) without affecting the myocardium. This may be accomplished using, for example, low energy/frequency RF or DC modulation/ablation, vibration energy selective for autonomics, as well as chemical, pharmaceutical or other agents.

Electrical Energy for Mapping, Sensing, Modulation and/or Ablation

In further accordance with one or more exemplary forms outlined herein, modulation/ablation may be accomplished through the use of AC or DC electrical energy to block nerve signals, stimulate nerve signals, or ablate nerve tissue. Signals from autonomic ganglia may be blocked by positioning electrodes or an array of electrodes in selected pericardial spaces such as the oblique sinus, the transverse sinus, or other pericardial spaces). The electrodes can be mounted on any one of the expandable element discussed herein to provide broad or dispersed coverage. It is also contemplated to use saline or other fluid to act as a virtual electrode in order to again provide broad or dispersed coverage, and to use containing elements of the type outlined herein in order to seal a given space to contain the treatment fluid.

When electrical energy is selected as the treatment medium the electrodes could provide high frequency AC signals to modulate, down-regulate or block signals on nerves or within ganglia. Further, the system may provide pulsed electric fields (PEF) to destroy nerve tissue (see U.S. Published Patent Application No. 20070265687). Direct current (DC) may be useful to selectively inactivate or destroy myelin and/or nonmyelinated nerves. The energy required to block/ablate is preferably chosen so as not to damage or modulate the myocardium.

Further, when electrical energy is selected as the treatment medium, the electrodes could provide high frequency AC signals to modulate, down-regulate or block signals on nerves or within ganglia; further, it could provide pulsed electric fields (PEF) to destroy nerve tissue (see U.S. Published Patent Application No. 20070265687). Direct current (DC) may be useful to selectively inactivate or destroy myelin and/or non-myelinated nerves—Energy required to block/ablate nerve without damaging or modulating myocardium.

The threshold for tissue destruction varies based on the type of tissue and its state of health. For example, nerve tissue has a different threshold for injury or ablation than cardiac muscle. Since our approaches involve modulation of tissue from the external surface the proximity itself of the nervous system related structures when compared to muscle allows an increased likelihood that the nervous tissue will be modified without necessarily resulting muscle damage. Further, certain energy forms such as low coulomb direct current energy rarely causes permanent muscle damage but frequency may result in temporary or permanent ablation of some types of peri-cardiac nerve tissue. Also for another example, nerve tissue itself may have different thresholds for injury. Myelinated fibers may be less susceptible to direct current or radiofrequency beams compared to non-myelinated fibers while the propensity for damage or ablation when using a chemical agent such as alcohol yields opposite results (myelinated fibers more susceptible than non-myelinated fibers). The assessment and deployment of energy delivery or chemicals can therefore be done in a manner to target specific types of tissue or within a group of tissue specific types of fibers depending on the type of heart rhythm or other cardiac disturbance being modulated. Thus, although the same regional autonomic fibers may be targeted with therapy based on the threshold to injury the type of energy delivered, whether or not DC current or RF energy or chemicals are used treatment can be individualized for rhythm disturbances versus decreasing cardiac pain.

One or more of the devices outlined herein provide electrodes in direct contact with ganglia or ganglia bundles, such as by mounting the electrodes one or more of the expandable elements discussed herein in order to achieve broad or dispersed surface coverage, or by mounting the electrodes in a dispersed array of independent wires such as is found in FIGS. 9 and 10. Further, the electrodes may effectively make in direct contact with the desired treatment area by exposing the electrodes to a hypertonic saline or other fluid delivered to the pericardial area, with the electrodes communicating alternating current (AC) and/or direct current (DC), thus turning the fluid into a "virtual electrode" which effectively contacts the nerve tissue to block or ablate/denervate a tissue (see any of the foregoing embodiments with infusion ports). The fluid fills the selected space and thus carries the DC or other electrical current to the selected area to either activate, block, or ablate nerve tissue/autonomics. This allows both broad field coverage and the ability to modulate nerve activity at a distance.

The electrodes or electrode arrays mentioned herein may be used to stimulate nerve tissue, or to stimulate receptors on cardiac tissue. The electrodes may be used to stimulate receptors on the atria, which when stimulated increase the sinus rate, and thus electrodes cold be placed in this region to stimulate and to pace the heart. The stimulating or blocking electrodes specifically designed to have preferential effects on the nerve fibers emanating from the cardiac ganglia and either inserting into the heart muscle or fibers that emanated from the heart muscle and will traverse one of the ganglias. However, these electrodes may also be used to target for the desired effect the ganglia themselves, the ganglia and underlying heart muscles, or in some instances unique transitional or receptor cells that form the interface between the nerve fibers and the heart muscles. In some instances unique transitional or receptor cells form the interface between the nerve fibers and the heart muscles.

The electrodes or electrode arrays mentioned herein may be used to down-regulate or block nerve tissue, or to modulate receptors on cardiac tissue. The electrodes may be used either directly or via receptors on the atria, which when blocked decrease the sinus rate, and thus electrodes could be placed in this region to control or reduce heart rate.

A stimulation threshold could be determined as a level at which there would be enough to activate ganglia, but not enough to activate the myocardium (either ventricular or atrial), and this approach would prevent the treatment from being proarrhythmic.

There may be a combination of electrical energy and a chemical agent to stun, block, or ablate autonomic tissue. This combination would allow for the targeting of autonomic tissue or cardiac pain fibers (e.g. relatively low-power energy and relatively low concentration of agent) without damaging myocardium as the nervous tissue will be more sensitive to these modulation means than will myocardium. Specific examples of such approaches include the use of low energy AC/DC/RF combined with alcohol. It may be preferable to use alcohol as the irrigating medium along with AC, DC or RF, since it may be desirable to use a low enough Ac and/or DC energy level solely for neuro-blocking or electrolysis, along with the alcohol for a similar effect. By changing the relative proportion of AC energy, DC energy, RF energy, and the alcohol irrigation could allow differential ablation of one specific component of either the autonomic nerves or the cardiac pain fibers.

The disclosed catheter and deliver systems outlined herein may be used to deliver energy or a chemical agent to stun, block, or ablate autonomics near the transverse sinus. Based on anatomy, it may be important in at least some applications to completely or nearly completely encircle the main pulmonary trunk, while still having a catheter seated in the transverse sinus. We thus envision a catheter/delivery assembly capable of placement within the transverse sinus, which may also have a blunt tip that is deflectable and extendable from the main catheter body. The extendable tip will be pushed forward and will course between the SVC and the main pulmonary artery trunk, lateral to the ascending aorta and circle anterior to the main pulmonary trunk. The catheter/delivery assembly may then clasp in a lasso or ring-like conformation around the medial or leftward portion of the main pulmonary arteries (see FIG. 14). This design would specifically be helpful for the sympathetic and other autonomic ganglia located in proximity to the superior vena cava and around the pulmonary trunk. This additional catheter/delivery assembly design could be an addition to the primary dual surface transverse sinus catheter described above with the extendable element extended to go completely around either or both of the great arterial trunks.

The delivery assembly may have multiple electrodes positioned along the length of the delivery tip, such as is seen in many of the foregoing Figures, order to create a bipolar field over which energy could be delivered between electrodes and thereby create a larger field in which to stun or ablate nerve tissue within the field. The stimulatory electrodes may be mounted on the expandable element as shown in numerous of the foregoing embodiments, or mounted on multiple independent wires as shown in FIGS. 9 and 10, and may be placed in the oblique sinus for high-rte stimulation of autonomic tone of the atria or in the region of the aorto-caval ganglion for atrial rate control and to treat ventricular fibrillation.

Mechanical Energy for Mapping, Sensing, Modulation and/or Ablation

The present device and method also contemplates modulation/ablation using mechanical energy. For example, the delivery assembly may use a piezoelectric element to perform one or more of a mapping function in order to find the autonomics, to stun the autonomics at a selected treatment areas, to assess the result of treatment, and to use vibrational energy created by the element to ablate or kill local autonomic activity at the selected treatment area. Ablation may also be performed using HIFU, AC or DC.

Other mechanical means may include the use of abrasion element or a blade device to perform a local neurectomy. The device may function to locate and/or orient the treatment delivery tip assembly and then mechanically disrupts the relevant tissue. Such a device may also include serrated/barbed edges, blades or other elements, which elements may be arranged to rotate against pericardial sac and/or against the epicardial wall of the atrium. Additionally, vibrational energy in the form of either piezoelectric vibration or mechanical vibration may be useful in order to terminate ventricular and/or atrial fibrillation.

Chemical Agents for Modulation and/or Ablation

The present device and method also contemplates the use of chemical agents for modulation, blocking, and/or ablation of autonomic nerve signaling. The delivery assembly may include a pump/reservoir system, which preferably utilizes the catheter, to deliver an agent into the pericardial space to block/stun, or kill/ablate nerve tissue. Exemplary devices could be placed by the subxyphoid approach, and may include an anchoring/stabilizing expandable element (balloon, nitinol, etc., of the exemplary forms discussed above, to prevent the device from slipping back into the thoracic cavity (see FIGS. 6-8, 11 and 13) A chemical delivery device infuses an agent through a port or array of diffusion ports, and could have additional ports for removing the agent and/or flushing the space with saline/water after the agent has been removed.

A supply source and/or a pump preferably is connected to the sensing array or system, and if arrhythmia is detected the system can dispense a suitable chemical agent into pericardial space or to another targeted treatment location. A suitable electrode sensor could be placed in the pericardial space, on the epicardial surface, within the myocardium, or on the skin to sense ECG signals or other signals to detect a cardiac disorder (e.g. arrhythmia). The system may then activate the pump in order to dispense the agent. Further, the could be dispensed from a catheter placed in any pericardial space (oblique sinus, transverse sinus, pericardial sac, etc.). The agent could be any agent that temporarily blocks nerve signaling such as, for example, Bupivocaine, lidocaine, a cooled fluid, procainamide, etc. The pump/reservoir could be located externally, or in the thoracic cavity, or subdermally (for ease of refilling).

A system employing a chemical agent and an associated pump, etc., could readily be combined with other means (e.g. instill the agent, and then use mechanical, thermal, or electrical means to further enhance modulation) In one exemplary embodiment, a selected space (pericardial, sinuses) could be instilled with saline which acts to carry RF, AC or DC energy to a large area. The space could be filled with alcohol and then energy could be delivered using one or more of the above-mentioned mechanisms, such as RF, AC, DC, etc., or mechanical means. Alternatively, one of the above-described expandable devices could be used and could contain both a sponge/mesh for delivering agent and also contain electrodes for delivering energy (see FIGS. 2 and 3 for example). Another contemplated version expands from a compressed state for delivery through the catheter and then shifts to an expanded, deployed state upon exiting the catheter (e.g. nitinol mesh/framework, balloon, foam, etc). The expanded device would provide greater surface area coverage for modulating the tissue and also could conform to a given space (e.g. oblique sinus or transverse sinus). The expanded device could contain or be covered by a sponge/fabric/foam which could retain the agent to be delivered to contain the agent to a given area (i.e. prevent damaging surrounding tissues) and also keep the agent at the area for a longer period of time (prevent the agent from being washed away).

The expanded device could contain or be covered with electrodes which could be used for mapping/orientation or for delivering energy to stun/kill/denervate nerve tissue. The catheter with an expandable element (mesh, sponge, foam) carrying a drug combination to a given pericardial space. In terms of specific drug combination, the use of a fixed mixture of procainamide along with an alpha-blocker such as phentolamine or phenoxybenzamine along with a viscous gel and alcohol. This could be exuded through the pores of the sponge-like element and, which in turn, is temporarily inserted in the pericardial space, to assess efficacy for a few days and then the same catheter/element set used for more permanent ablation either by an injection of a greater strength of the same agents, different agents, or the combination of agents and electrical energy (RF, AC or DC) using electrodes mounted on the expandable element.

Pump/system could be used acutely (fill space with agent—treat—then remove device) or chronically (implantable pump system to periodically deliver agent or deliver agent based on actuation by sensor component). Pump (catheter version) could have an expandable element(s) that attaches to or protrudes from catheter (balloon/nitinol mesh/foam) which expand and can contain the delivered agent to a given space (see FIG. 13). Pump (catheter version) could have means to provide orientation of the device within a given space. Orientation could be provided by differential coatings (e.g. one side of the catheter is coated with an echogenic or radiopaque coating that could be seen by ultrasound or x-ray respectively. Alternatively, orientation could be provided by electrodes on the catheter or on a device that protrudes from the catheter. (See FIG. 5).

For treatment in the Transverse Sinus, the catheter would be oriented to place the electrodes in contact with myocardium. This would allow the operator to receive an ECG signal from the myocardium and know that the catheter is correctly oriented. The operator could then infuse an agent directionally to ablate, block autonomics on the pericardial sac (away from the surface of the heart) (see FIGS. 6-8). For treatment in the Oblique sinus, the catheter would be positioned opposite that of the transverse sinus (i.e. electrodes against the pericardial sac such that no ECG signals are seen). Catheter placed around the ventricles to deliver an agent and/or energy to block, stun, or ablate cardiac pain fibers to treat chronic intractable chest pain (see FIG. 6). A pump/catheter could deliver agents to stun or temporarily block nerve activity such as Trimethophan, Quinadine, Procanamide, Bupivocaine, Phenoxybenzamine, Phentolamine, Anticholinergics, Alpha and Beta Blockers, Hexamethonium, Pentolinium, Mecamylamine, Pempidine, and could also deliver agents to permanently ablate/destroy/block nerve activity such as Phenol, Ethanol, Ammonium Salts, Phenoxybenzamine, Formalin.

Specific electrodes designs are contemplated for alcohol±DC current applications. A sponge-like electrode made of, for example, non-nitional components that may be expanded and placed in the oblique sinus so that true small ports alcohol can be effused and the non-nitinol segments will absorb any leakage preventing and/or minimizing more widespread effects. The same course may have electrodes which permit placement of RF current or DC current or electrolytic doses of DC current to produce maximal effects of the alcohol on the ganglia in positions of contact.

Thermal Modulation and/or Ablation

Thermal or radiofrequency means may be used to perform modulation/ablation. Ablation of receptors on the ventricle may be used to increase the sinus rate, and thus the device may function as a pacemaker. The ablation of subepicardial ventricular receptors may also be performed, as can RF ablation with saline as virtual electrode (See FIGS. 2-8. Cryogenic energy can be used to cool the epicardial surface/pericardium of the heart (both autonomics and/or myocardium) to terminate arrhythmias. This could form the basis of painless defibrillation. Cooling could be accomplished by several means, such as the injection of cooled fluid into pericardial space or into device placed in contact with atria or ventricle or ganglia. A cooling of mesh may be brought into contact with the heart (e.g. by use of Peltier type system as outlined in U.S. Pat. No. 5,515,682). Chemicals which mix and cause an endothermic reaction could be used, as can cenergy to transiently block signaling/ablate nerve tissue. Cryogenic catheters would be positioned as described above for placement in the transverse sinus or oblique sinus. Transverse sinus, the cryogenic source would be oriented away from the epicardial surface of the heart, and towards the epicardial surface of the heart in the oblique sinus. Electrodes mounted on the cryogenic catheter could be used to orient the catheter correctly (See FIGS. 15-18). Operators may perform cryogenic cooling for atrial fibrillation (relatively slow cooling) with a device that protects the esophagus (see FIG. 18), which offers large surface covering and rapid cooling for ventricular fibrillation.

Cooled saline or other refrigerants may be used. In accordance with one exemplary aspect, cooling can be used as part of an implanted system which is left in the body using the type of sheath described above to prevent leakage. One contemplated method is an endothermic reaction that would occur on contact, and which may cause an immediate or near immediate and relatively sudden cooling. When this cooling occurs arrhythmia may be suppressed both because of the effects of the cooling on the autonomics and perhaps due to the effects of cooling on the ventricular myocardium itself. This approach would in fact be a type of cryo manipulation. In addition, a contemplated approach envisions this cooling can be done temporarily and regionally, i.e., not for the whole heart but at specific chosen locations, such as the ganglia behind the atrium.

Modulation of the cardiac autonomics, interventricular myocardium, or the receptors/transitional regions between nerve fiber and myocardium may be used for non-arrhythmia indications. These include control of cardiac chest pain, modulation of cardiac activity and contractions, or in some instances to increase the heart rate. In some cardiac conditions such as neurocardiogenic syncope there is over activity of some of the mechanoreceptors that modulate a reflex designed to prevent over vigorous cardiac contractions. An untoward effect of activities from these receptors is inordinate lowering of the blood pressure or slowing of the heart rate. The methods described may be used to target these receptors or the nerves that originate in these receptors where by the abnormally low heart rate may be modulated to increase potentially obviating the need for a pacemaker in some instances. On the other hand, these same receptors may also be dysfunctional and create abnormally high heart rates and blood pressure and either stimulation blocking or ablation of these receptors may be helpful in reducing these abnormalities as well.

In accordance with one or more of the aspects outlined herein, treatment methods and treatment devices may be viewed in modular form. These modules include options for accessing the relevant space or treatment are, options for mapping and/or identifying the ganglia or autonomic nervous system activity, options for modulating the ganglia of other autonomics, and options for interpreting and/or assessing the results of the modulation.

For example, the options for accessing and/or covering the desired or selected treatment area include accessing any one or more of the pericardial space (e.g. subxyphoid access, thoracotomy), the epicardial surface, the oblique sinus, the transverse sinus, retro-atrial area, or broad field coverage (cover a relatively large area to get all ganglia or broad ganglia coverage, which can be spread out over a relatively large area).

The options for mapping and/or identifying the ganglia activity or other autonomic nervous system activity include the algorithms and filtering discussed above regarding various aspects of distinguishing and/or matching eletrogram morphology. Further options exist, such as may be found in *Feasibility Study of Endocardial Mapping of Ganglionated Plexuses During Catheter Ablation of Atrial Fibrillation*, Lemery et al., Heart Rhythm Society, (1996); *Combined Effect of Pulmonary Vein Isolation and Ablation of Cardiac Autonomic Nerves for Atrial Fibrillation*, Ohkubo et el., (2008); and in *Gross and Microscopic Anatomy of the Human Intrinsic Cardiac Nervous System*, Armour et al., The Anatomical Record, 247:289-298 (1997).

Further, the various mechanisms or means for modulating and/or ablating nervous system activity may be selected from any one of the foregoing mechanisms or means. For example, one may choose electrical means, such as, for example, alternating or direct current energy, for stimulation and blocking of activity. Mechanical options also may be chosen such as, for example, ultrasound, vibration, or other physical disruption or application of kinetic energy. Chemical means may be chosen from any one of the foregoing discussed examples, and thermal means may be chosen, again from any one of the foregoing discussed examples, including heating, cooling, cryogenic and/or RF energy.

Finally, the options for assessing and/or interpreting the results of the modulation include mapping of the relevant nervous system or autonomic activity after the treatment step. These options would also include assessing and/or interpreting indirect results of the modulation step such as, for example, surrogate biological functions including heart rate, blood pressure, etc.

Is used herein, autonomic activity and/or autonomic regulation may be used to refer to any of the ganglia activity or nervous system activity discussed herein. Therefore, it may be convenient to use the term autonomics to apply generically to these various types of activity. These specific types of activity are mentioned for explanatory purposes only, and are not intended to limit in any way the scope of the claims appended hereto.

Numerous modifications and alternative embodiments of the invention will be apparent to those skilled in the art in view of the forgoing description. Accordingly, this description is to be construed as illustrative only and is for the purpose of teaching those skilled in the art the best mode of carrying out the invention. The details of the present disclosure may be varied without departing from the spirit of the invention, and the exclusive use of all modifications which are within the scope of the claims is reserved.

The invention claimed is:

1. A device for modulating an autonomic nervous system adjacent a pericardial space to treat cardiac arrhythmia, the device comprising:
 a treatment source arranged to supply a treatment medium;
 a catheter having a proximal end and a distal end, the distal end sized for insertion into the pericardial space;
 a medium delivery assembly, the medium delivery assembly having a proximal end and a distal end, the distal end of the medium delivery assembly arranged to be positioned by the distal end of the catheter, the distal end of the medium delivery assembly comprising a delivery tip arranged to extend away from the distal end of the catheter into the pericardial space; and
 a connector operatively coupling the delivery tip of the medium delivery assembly to the treatment source, wherein the delivery tip of the medium delivery assembly includes: (i) a plurality of delivery points for delivering the treatment medium at a plurality of treatment areas within the pericardial space and (ii) a fluid retention element, and
 wherein the fluid retention element comprises a fabric material, a sponge, or foam that is configured to hold the treatment medium in a confined area after the treatment medium is delivered from the plurality of delivery points.

2. The device of claim 1, wherein the plurality of delivery points for delivering the treatment medium includes a plurality of electrodes.

3. The device of claim 2, wherein the plurality of electrodes is disposed on an expandable portion, the expandable portion shiftable between a collapsed state and an expanded state.

4. The device of claim 3, wherein the expandable portion is covered with the fluid retention element.

5. The device of claim 3, wherein the expandable portion comprises an expandable metal material, the expandable portion secured in the collapsed state by a removable sheath.

6. The device of claim 3, wherein the plurality of electrodes are disposed only on a single side of the expandable portion to facilitate directional deployment of the treatment medium.

7. The device of claim 6, wherein the expandable portion is covered by a polymer cover in an orientation to facilitate the directional deployment of the treatment medium.

8. The device of claim 3, wherein the device comprises a reservoir, and including a conduit providing flow communication between the reservoir and the delivery tip.

9. The device of claim 8, wherein the delivery tip comprises a plurality of exit apertures in fluid communication with the conduit, and wherein the exit apertures are disposed on an expandable portion.

10. The device of claim 9, wherein the expandable portion comprises an expandable metal material, the expandable portion secured in the collapsed state by a removable sheath.

11. The device of claim 1, wherein the expandable portion is covered by a polymer cover in an orientation to facilitate directional deployment of the treatment medium.

12. A device for modulating an autonomic nervous system adjacent a pericardial space to treat cardiac arrhythmia, the device for use with a steerable catheter having a central lumen, a proximal end, and a distal end sized for insertion into the pericardial space, the device comprising:

a treatment delivery assembly, the treatment delivery assembly having a proximal end and a distal end, the distal end of the treatment delivery assembly arranged to extend from the distal end of the catheter and into the pericardial space;

the distal end of the treatment delivery assembly comprising an expandable delivery tip with a plurality of delivery points for delivering a treatment medium within the pericardial space, the expandable delivery tip being shiftable between a collapsed state and an expanded state;

a source of the treatment medium;

a connector operatively coupling the expandable delivery tip to the source of the treatment medium; and a fluid retention element attached to the expandable delivery tip and comprising a fabric material, a sponge, or foam, that is configured to hold the treatment medium in a confined area within the pericardial space after the treatment medium is delivered from the plurality of delivery points.

13. The device of claim 12, wherein the plurality of delivery points for delivering the treatment medium comprises an array of electrodes.

14. The device of claim 12, wherein the array of electrodes are disposed on metal frame members.

15. The device of claim 14, wherein the array of electrodes are disposed only on a single side of the expandable delivery tip to facilitate directional deployment of the treatment medium.

16. The device of claim 12, wherein the expandable portion is covered with a polymer cover in an orientation to facilitate directional deployment of the treatment medium.

17. The device of claim 12, wherein the expandable delivery tip is covered with the fluid retention element.

* * * * *